US007250029B2

(12) United States Patent
Fujita et al.

(10) Patent No.: US 7,250,029 B2
(45) Date of Patent: *Jul. 31, 2007

(54) HUMAN CONDITION EVALUATION SYSTEM, COMPUTER PROGRAM, AND COMPUTER-READABLE RECORD MEDIUM

(75) Inventors: Etsunori Fujita, Hiroshima (JP); Yumi Ogura, Hiroshima (JP); Naoki Ochiai, Hiroshima (JP); Yasunori Noto, Fukuoka (JP); Tiejun Miao, Fukuoka (JP); Toshiyuki Shimizu, Fukuoka (JP)

(73) Assignee: Delta Tooling Co., Ltd., Hiroshima (JP)

( * ) Notice: Subject to any disclaimer, the term of this patent is extended or adjusted under 35 U.S.C. 154(b) by 414 days.

This patent is subject to a terminal disclaimer.

(21) Appl. No.: 10/849,685

(22) Filed: May 20, 2004

(65) Prior Publication Data
US 2004/0236235 A1    Nov. 25, 2004

(30) Foreign Application Priority Data
May 21, 2003  (JP) .............................. 2003-180294

(51) Int. Cl.
*A61B 5/00*    (2006.01)
*A61B 5/02*    (2006.01)
*A61B 5/08*    (2006.01)
(52) U.S. Cl. ..................... 600/300; 600/485; 600/500; 600/504; 600/529; 600/534
(58) Field of Classification Search .................... None
See application file for complete search history.

(56) References Cited

U.S. PATENT DOCUMENTS 5,846,206 A * 12/1998 Bader .......................... 600/534
2002/0089425 A1* 7/2002 Kubo et al. ................ 340/573.1

* cited by examiner

*Primary Examiner*—Charles A. Marmor, II
*Assistant Examiner*—Patricia Mallari
(74) *Attorney, Agent, or Firm*—Wolf Block Schorr & Solis-Cohen LLP

(57) ABSTRACT

A human condition evaluation system, of which bio-signal analysis means includes a bio-signal peak value detection means for detecting a peak value for each cycle of an original waveform of a bio-signal data, and a power value calculation means for calculating a difference between the peak value at an upper limit side and the peak value at a lower limit side for every prescribed time range using respective peak values obtained by the bio-signal peak value detection means to thereby set the difference as a power value, is structured to determine a predictive signal for falling asleep from an active state into a sleep state. Different from conventional human condition evalution based simply on a Lyapunov exponent as an indicator, a new human condition evaluation system based on a functional status of an energy generation system of the living body is provided.

16 Claims, 17 Drawing Sheets

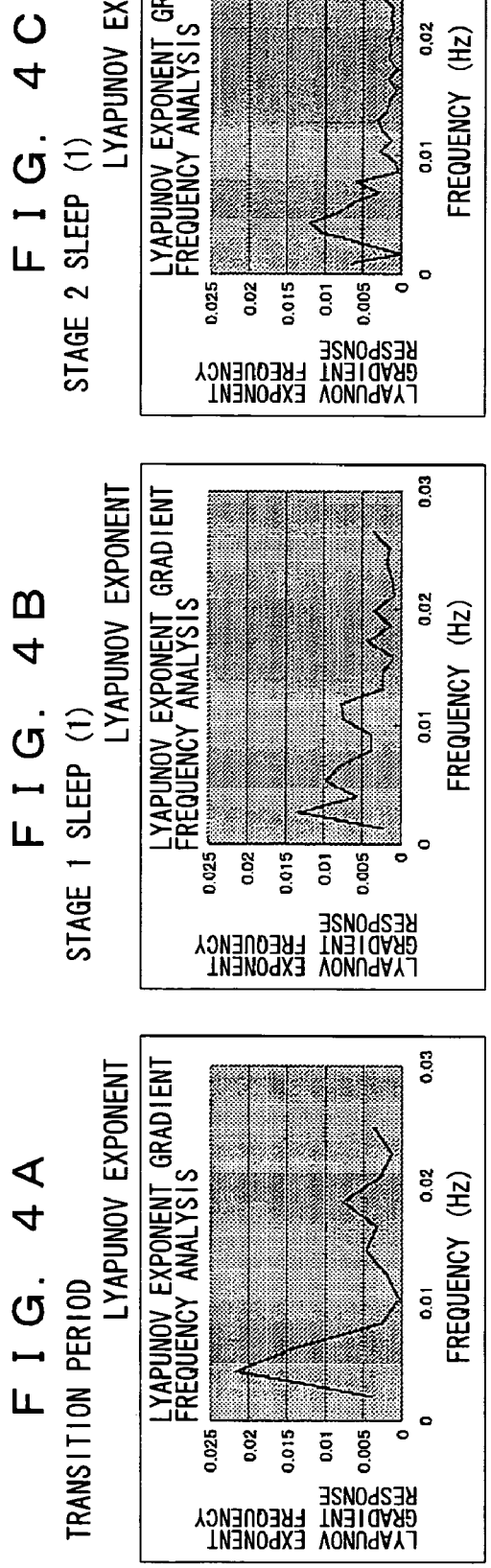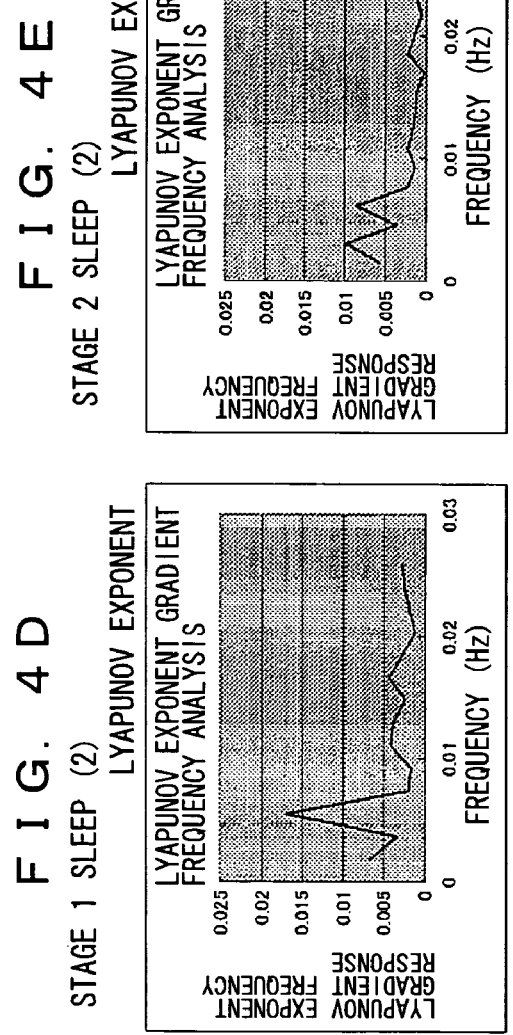

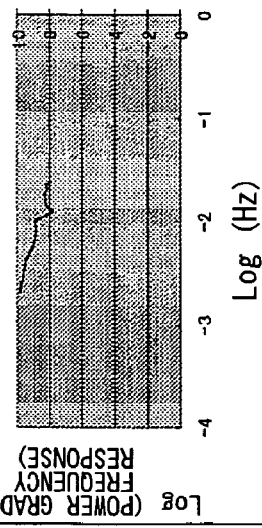
FIG. 5A — TRANSITION PERIOD — 1/F FLUCTUATION GRADIENT β=1.801
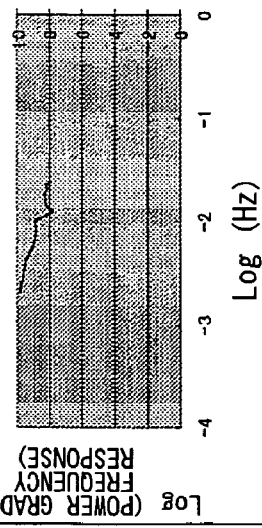
FIG. 5B — STAGE 1 SLEEP (1) — 1/F FLUCTUATION GRADIENT β=3.008
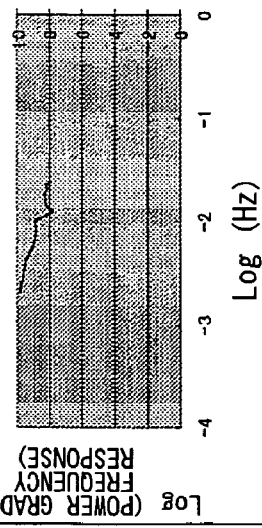
FIG. 5C — STAGE 2 SLEEP (1) — 1/F FLUCTUATION GRADIENT β=1.751
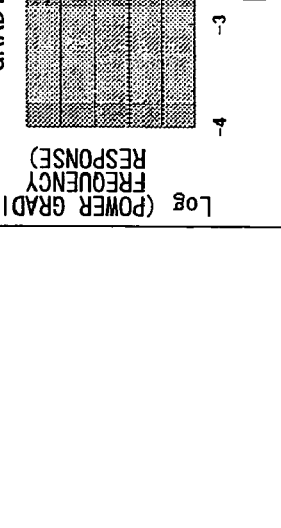
FIG. 5D — STAGE 1 SLEEP (2) — 1/F FLUCTUATION GRADIENT β=2.476
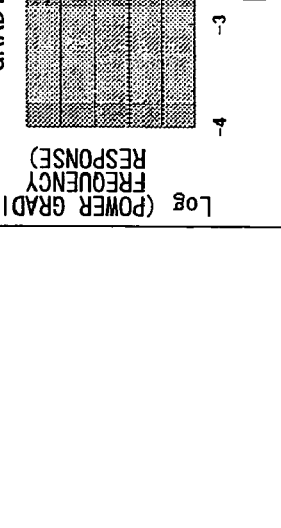
FIG. 5E — STAGE 2 SLEEP (2) — 1/F FLUCTUATION GRADIENT β=1.468

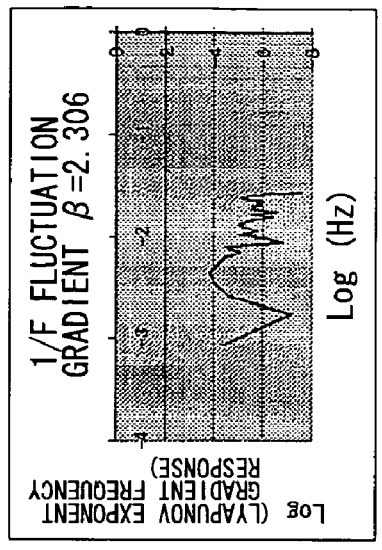
FIG. 6A
TRANSITION PERIOD
LYAPUNOV EXPONENT
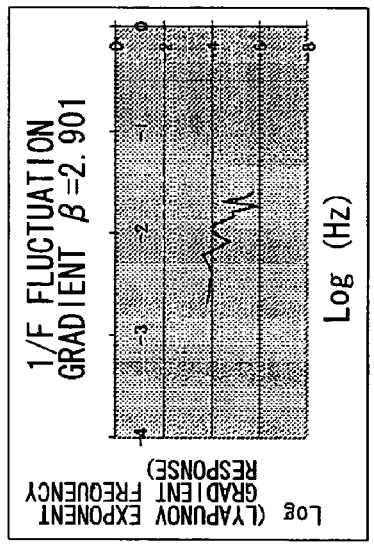
FIG. 6B
STAGE 1 SLEEP (1)
LYAPUNOV EXPONENT
FIG. 6C
STAGE 2 SLEEP (1)
LYAPUNOV EXPONENT
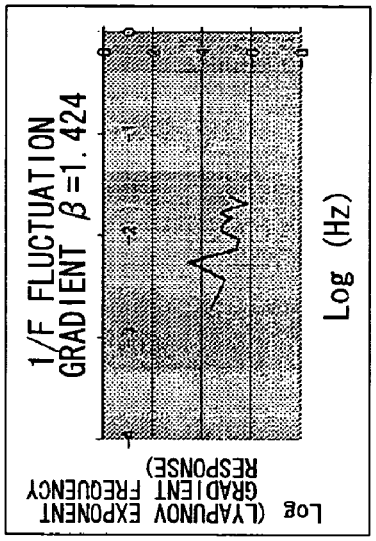
FIG. 6D
STAGE 1 SLEEP (2)
LYAPUNOV EXPONENT
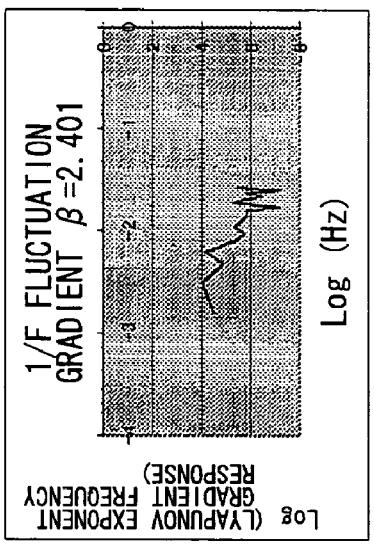
FIG. 6E
STAGE 2 SLEEP (2)
LYAPUNOV EXPONENT

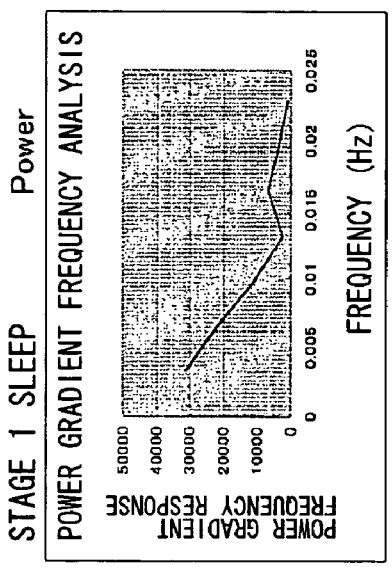
FIG. 8A REST STATE
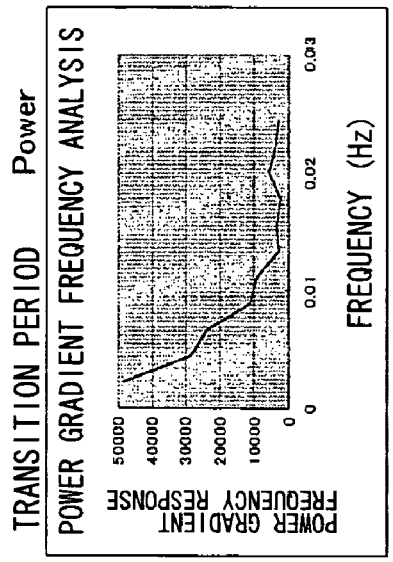
FIG. 8B TRANSITION PERIOD
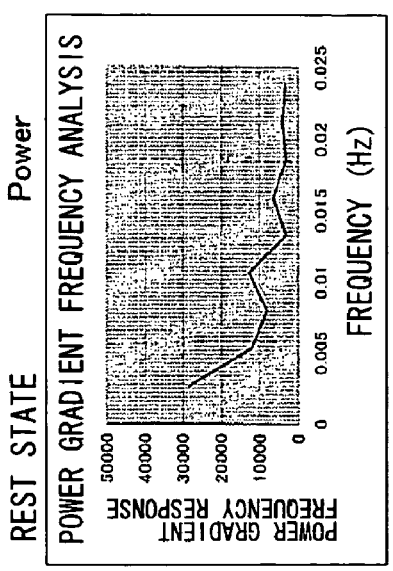
FIG. 8C STAGE 1 SLEEP
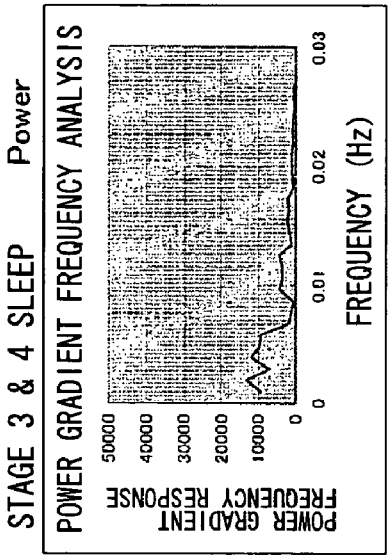
FIG. 8D STAGE 2 SLEEP
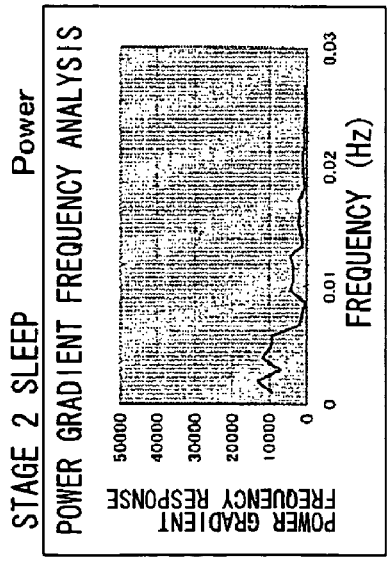
FIG. 8E STAGE 3 & 4 SLEEP

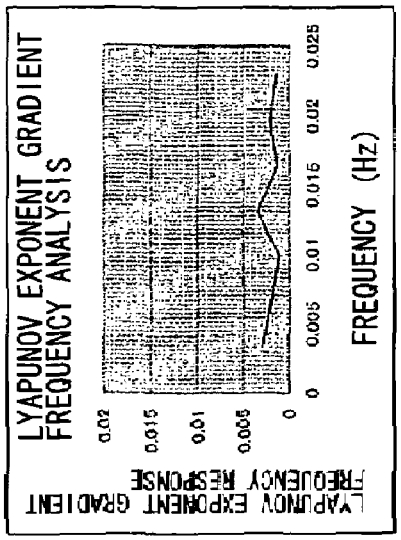
FIG. 9A REST STATE LYAPUNOV EXPONENT
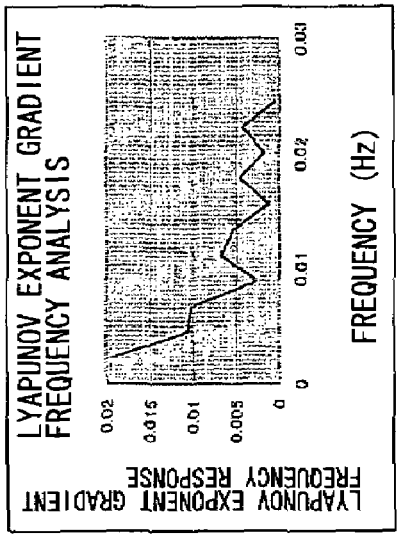
FIG. 9B TRANSITION PERIOD LYAPUNOV EXPONENT
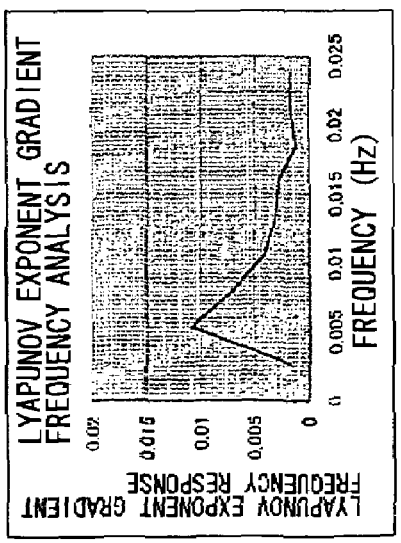
FIG. 9C STAGE 1 SLEEP LYAPUNOV EXPONENT
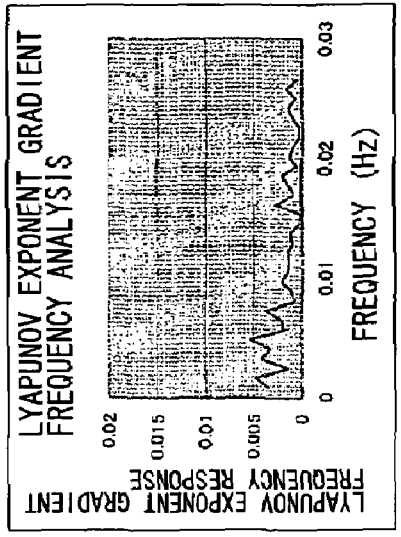
FIG. 9D STAGE 2 SLEEP LYAPUNOV EXPONENT
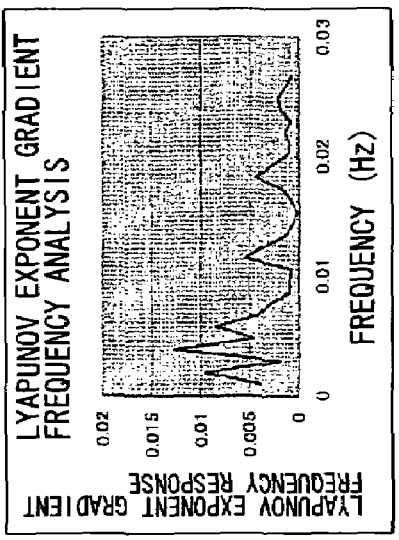
FIG. 9E STAGE 3 & 4 SLEEP LYAPUNOV EXPONENT

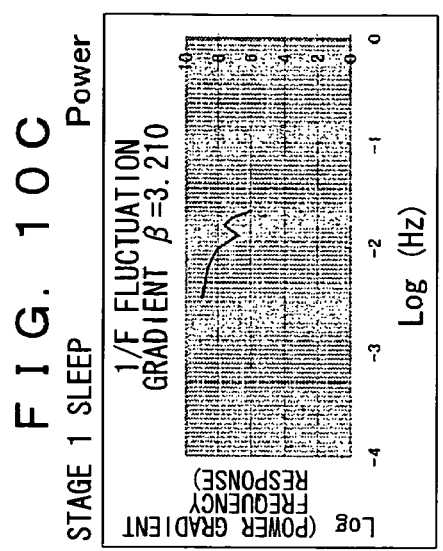
FIG. 10A REST STATE
1/F FLUCTUATION GRADIENT β=1.924
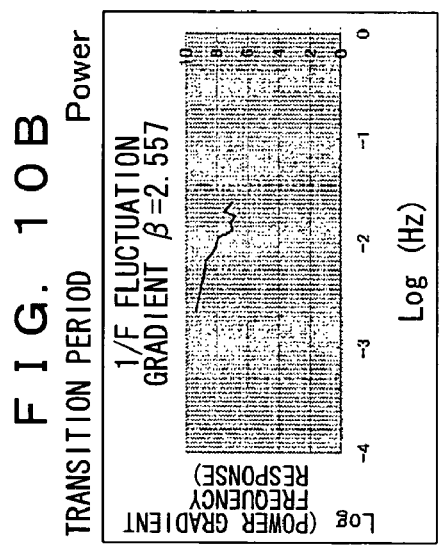
FIG. 10B TRANSITION PERIOD
1/F FLUCTUATION GRADIENT β=2.557
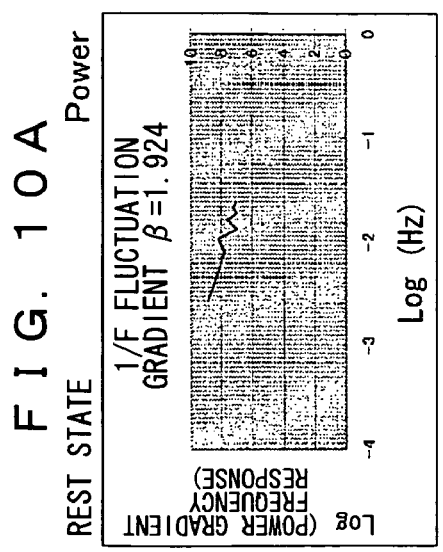
FIG. 10C STAGE 1 SLEEP
1/F FLUCTUATION GRADIENT β=3.210
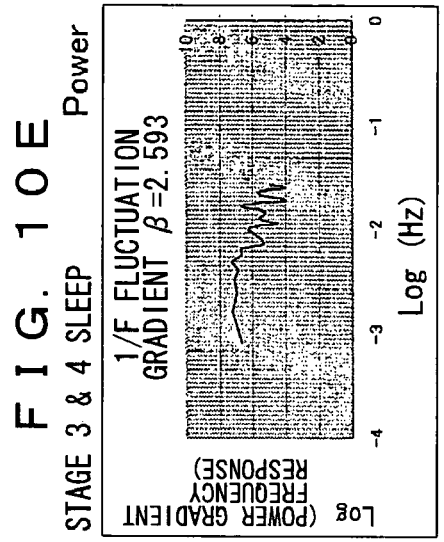
FIG. 10D STAGE 2 SLEEP
1/F FLUCTUATION GRADIENT β=2.322
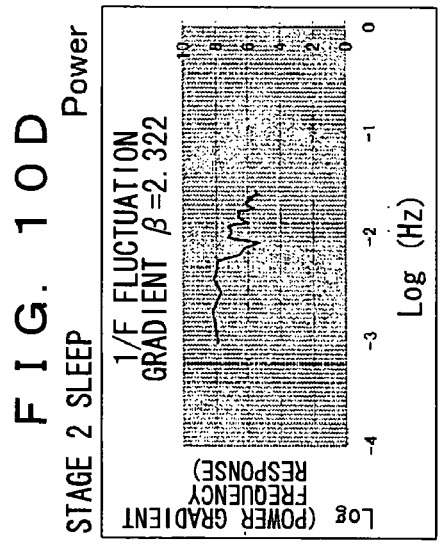
FIG. 10E STAGE 3 & 4 SLEEP
1/F FLUCTUATION GRADIENT β=2.593

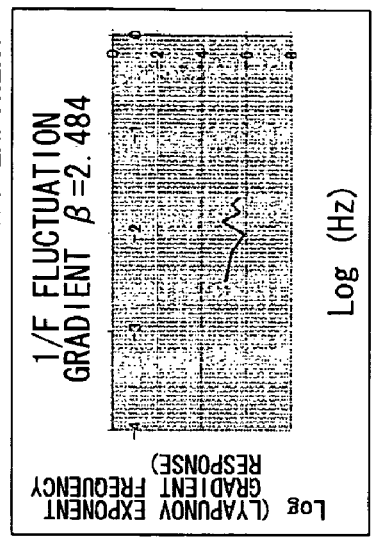
FIG. 11A  REST STATE
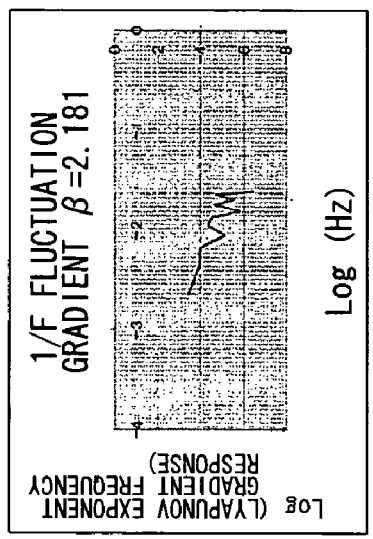
FIG. 11B  TRANSITION PERIOD
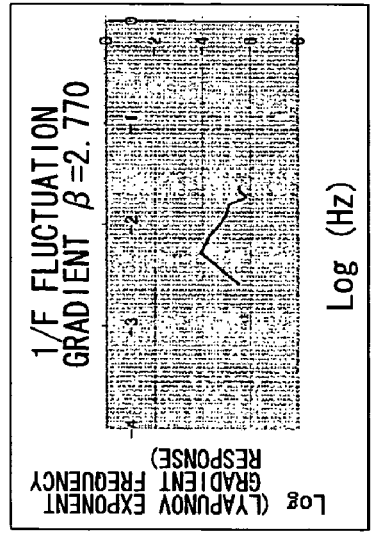
FIG. 11C  STAGE 1 SLEEP
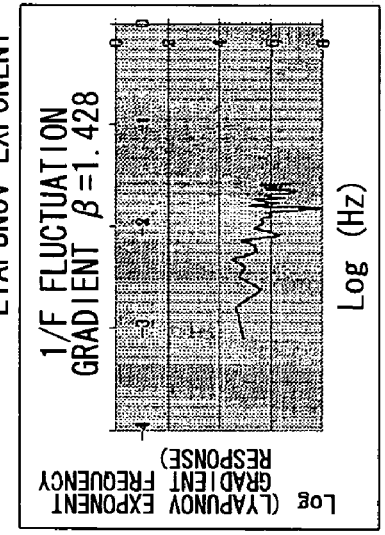
FIG. 11D  STAGE 2 SLEEP
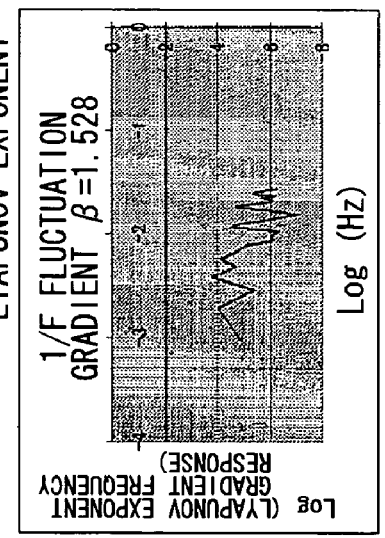
FIG. 11E  STAGE 3 & 4 SLEEP F I G. 1 3 A
TRANSITION PERIOD     Power
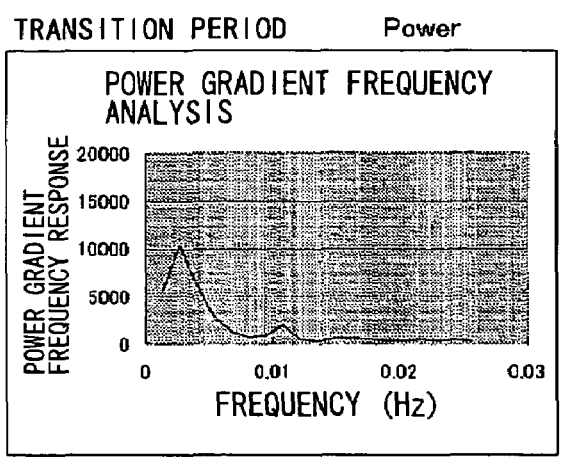
F I G. 1 3 B
STAGE 1 SLEEP (1)     Power
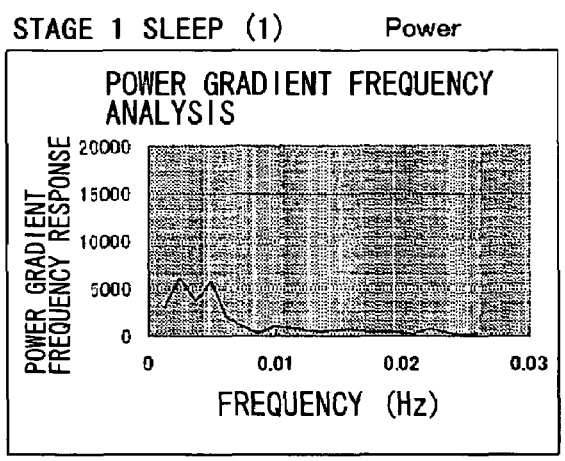
F I G. 1 3 C
STAGE 2 SLEEP (1)     Power
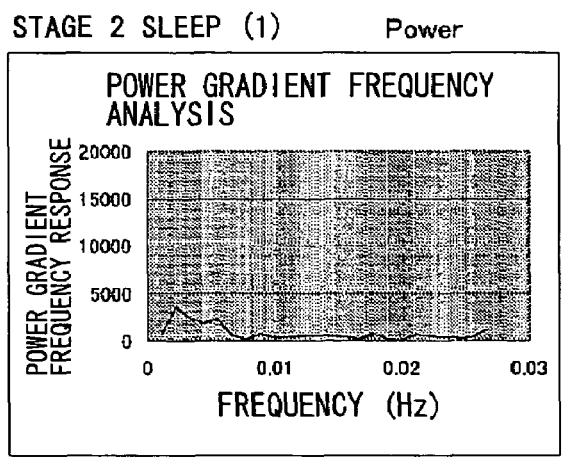
F I G. 1 3 D
STAGE 1 SLEEP (2)     Power
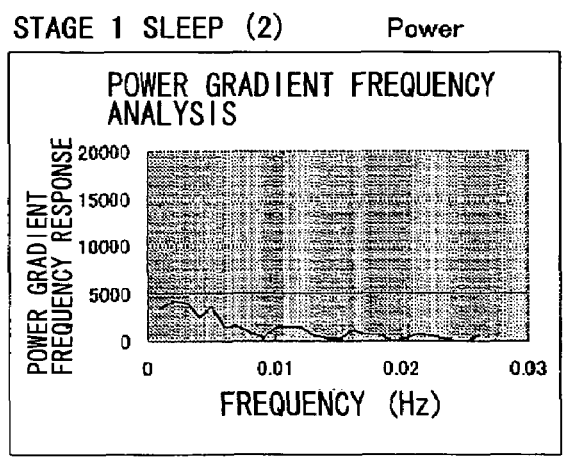

F I G. 1 4 A
TRANSITION PERIOD
LYAPUNOV EXPONENT
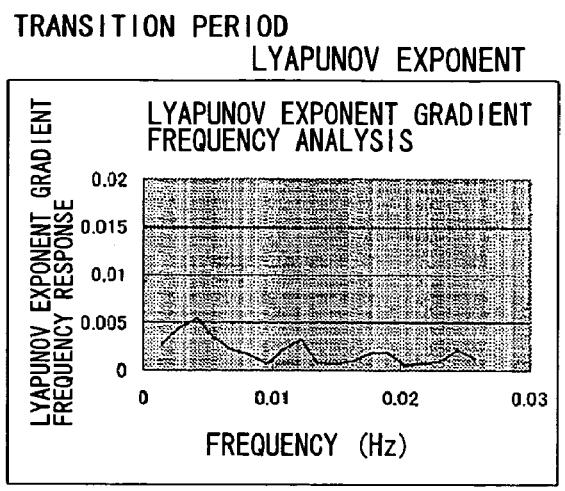
F I G. 1 4 B
STAGE 1 SLEEP (1)
LYAPUNOV EXPONENT
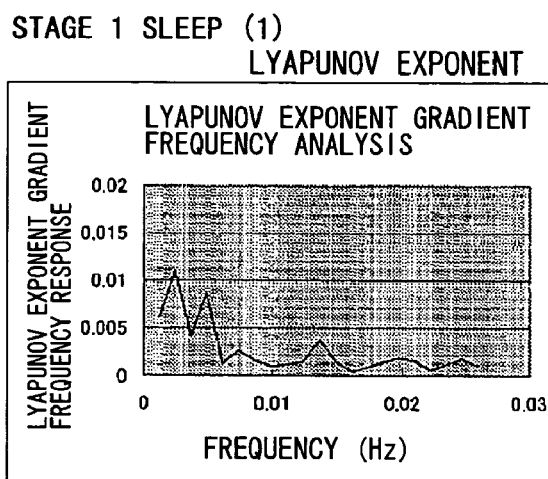
F I G. 1 4 C
STAGE 2 SLEEP (1)
LYAPUNOV EXPONENT
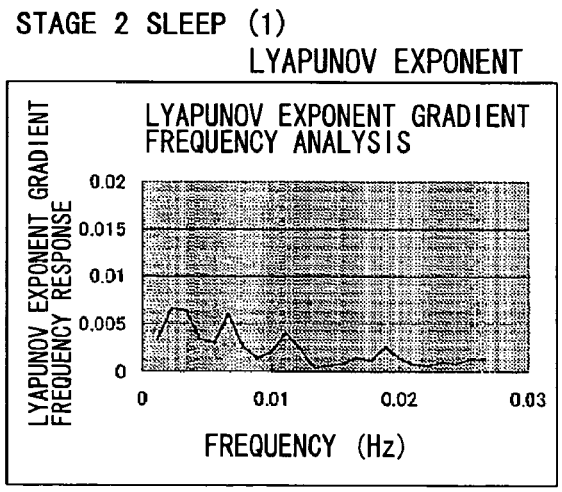
F I G. 1 4 D
STAGE 1 SLEEP (2)
LYAPUNOV EXPONENT
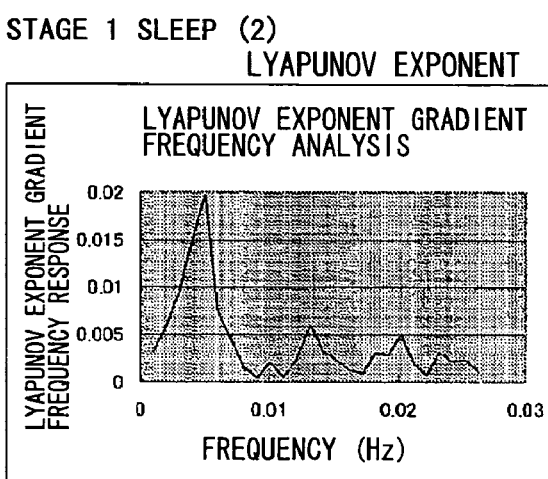

TRANSITION PERIOD  Power

STAGE 1 SLEEP (1)  Power

STAGE 2 SLEEP (1)  Power

STAGE 1 SLEEP (2)  Power

TRANSITION PERIOD

TRANSITION PERIOD

STAGE 1 SLEEP

STAGE 2 SLEEP

HUMAN CONDITION EVALUATION SYSTEM, COMPUTER PROGRAM, AND COMPUTER-READABLE RECORD MEDIUM

FIELD OF INVENTION

The present invention relates to a system for evaluating a human condition, and more particularly, to a human condition evaluation system and a computer program for detecting a transition from an active state to a sleep state of a human, and a record medium in which the computer program is recorded.

BACKGROUND OF THE INVENTION

For detecting a human condition whether he/she is in the active state (wakeful state or awakening state) or in the sleep state, conventionally, a brain wave measurement and a pattern analysis on the brain wave are conducted. However, the brain wave measurement has to be conducted under conditions limiting a person's normal movement, for instance, a brain wave electrode and/or an eletrooculographic electrode is/are required to be set on a head of a subject, and so forth. Therefore, when operating a vehicle such as an automobile, a train, and the like, it is difficult to evaluate the human condition without imposing a strain on the subject.

Meanwhile, as a traffic accident prevention measure, a monitoring of the human condition (psychosomatic condition) of a driver in operation is receiving attention in recent years. For instance, techniques for monitoring the human condition using a heart beat or a pulse are proposed in patent document 1 (Japanese Patent Application Laid-Open No. Hei 9-308614) and patent document 2 (Japanese Patent Application Laid-Open No. Hei 10-146321). According to the techniques disclosed in patent documents 1 and 2, no large-scale setting of equipment is required for measuring brain wave, whereby facilitating the evaluation of the human condition of the driver.

The devices disclosed in patent documents 1 and 2 both determine a psychosomatic condition of the driver using a chaos indicator calculated from the heart beat or the pulse. Specifically, they are structured to calculate a Lyapunov exponent from the heart beat or the pulse, as one chaos indicator, and when the Lyapunov exponent shows, in its time-series change, a decline beyond a prescribed time, it is determined to be just before falling asleep (a state feeling drowsy) due to a stress suffered and at a level requiring a rest. It is already disclosed in Japanese Patent Application Laid-Open No. Hei 4-208136 that the chaos indicator of a bio-signal enables objective diagnosis of a human condition. It is therefore presumable that the devices disclosed in patent documents 1 and 2 are capable of detecting the state just before falling asleep.

However, in patent documents 1 and 2, the disclosure is made for the determination of a fatigue state feeling drowsy only by the chaos indicator such as a Lyapunov exponent and the like, in which, in an attempt to determine the fatigue state feeling drowsy, a process reaching to a psychologically stabilized state is detected based on the declining change of the Lyapunov exponent, and in which the heat beat or the pulse measured is processed only for the chaos indicator.

Generally, a physical capability can be divided into that for survival, which is required for maintaining a life, and that for activity, which is supported by the former. The physical capability for survival corresponds to a capability to maintain life and health, and is referred to as defensive physical capability, while the physical capability for activity is a behavioral physical capability for moving a body, and is generally understood as athletic ability. A function for supporting the physical capability for activity includes an energy generation system, an energy supply system, and an energy control system. The energy generation system functions for a muscular system measured by muscular strength, staying power, and the like, which causes a muscle fatigue. The energy supply system functions for a respiration and circulatory system measured by oxygen uptake and heart rate. The energy control system functions for alterness, cooperativeness, balance, and adoptability. Consequently, the functional status of the energy generation system causing muscle fatigue can be known by analyzing the state of the energy supply system or the energy control system.

Now, by obtaining the Lyapunov exponent of a bio-signal data, the state of the energy control system can be known, and by measuring a resistance force (power value) obtainable from a peak value for each cycle of the bio-signal, the state of the energy supply system can be known. Accordingly, with the use of the Lyapunov exponent or the power value, which are obtainable from the bio-signal data, the functional status of the energy generation system can be known. However, as mentioned before, currently, only the Lyapunov exponent is paid attention, and the power value is not within the scope for understanding the functional status of the energy generation system.

For more detail, as a characteristic of a fatigue state feeling drowsy, the Lyapunov exponent sometimes shows a sharp downward trend, in other cases, a change in the power value can be seen sometimes more remarkable than the change in the Lyapunov exponent due to functional capability down of the energy supply system caused by energy release under the active state. Such a difference in change patterns largely depends on individual differences or health conditions. Therefore, for detecting an emergence of the fatigue state feeling drowsy more properly, the time-series change in the Liapunov exponent being an indicator of the state of the energy control system, and the time-series change in the power value being an indicator of the state of the energy supply system, are preferably used together in the system instead of using one.

In other words, the wakeful state or awakening state (active state) is a state psychologically stimulated and consuming higher calories, and when falling asleep, a person experiences a state psychologically relaxed but consuming still higher calories to reach to a state psychologically relaxed and consuming lower calories, or experiences a state psychologically stimulated but consuming lower calories to reach to the state psychologically relaxed and consuming lower calories. A typical sign indicating the former state psychologically relaxed but still consuming higher calories is an apparent decline in the Lyapunov exponent, and a typical sign indicating the latter state psychologically stimulated but consuming lower calories is an apparent decline in the power value. Based on this perspective, again, it is preferable to detect both the Lyapunov exponent and the power value instead of detecting one.

Further, in patent documents 1 and 2, the values of the Lyapunov exponent and the heart rate track the time-series changes thereof, while the value is detected for every 15 minutes or 30 minutes. Therefore, it is difficult to monitor the change in state substantially in real time, as required for a monitoring while driving.

OBJECTS AND SUMMARY OF THE INVENTION

The present invention is made in view of the above-described considerations, and an object of the present invention is to provide a human condition evaluation system and a computer program suitable for evaluating a human condition especially of a driver, which are capable of determining a predictive signal for falling asleep from an active state to a sleep state more accurate than ever by focusing attention also on a time-series change in a power value of a bio-signal in addition to a time-series change in a Lyapunov exponent of the bio-signal, and a record medium in which the computer program is recorded.

More specifically, according to the present invention a human condition evaluation system composed of a bio-signal analysis means for analyzing a bio-signal data detected by a bio-signal measurement instrument for measuring a bio-signal of a human, in which the bio-signal analysis means includes a bio-signal peak value detection means for detecting a peak value for each cycle of an original waveform of the bio-signal data, a power value calculation means for calculating a difference between the peak value at an upper limit side and the peak value at a lower limit side for each prescribed time range using respective peak values obtained by the bio-signal peak value detection means to thereby set the difference as a power value, a gradient calculation means for obtaining a gradient of the power value with regard to time base in a certain time range by performing slide calculation a prescribed number of times at a prescribed overlap rate with regard to the prescribed time, and a comparative determination means for comparatively determining whether a sudden drop state of the gradient of the power value exists or not in time-series change in the gradient of the power value obtained by performing the slide calculation to thereby determine the time range in which the sudden drop state appears to be a predictive signal for falling asleep from the active state into the sleep state, is provided.

According to the present invention a human condition evaluation system in which the bio-signal analysis means includes a Lyapunov exponent calculation means for calculating a Lyapunov exponent by performing chaos theory analysis on the bio-signal data, and a Lyapunov exponent peak value detection means for detecting a peak value for each cycle of a time-series change waveform of the Lyapunov exponent calculated by the Lyapunov exponent calculation means, in which the gradient calculation means includes a means for obtaining, in addition to the gradient of the power value, a gradient of respective peak values of the Lyapunov exponent with regard to time base in a certain time range obtained by the Lyapunov exponent peak value detection means, and in which the comparative determination means comparatively determines whether a sudden drop state exists or not in at least one of the time-series changes in the gradients of the power value and the Lyapunov exponent obtained by performing the slide calculation to determine a range in which the sudden drop state appears to be the predictive signal for falling asleep for the falling asleep from the active state into the sleep state, is provided.

According to the present invention a human condition evaluation system in which the comparative determination means compares the time-series changes in the gradients of the power value and the Lyapunov exponent which are obtained by performing the slide calculation with the gradient calculation means, and determines whether the gradients of the power value and the Lyapunov exponent are in opposite phases with each other or not before or in the range in which the sudden drop appears in the gradient of the power value or in the gradient of the Lyapunov exponent, and in the case where the sudden drop in the gradient of the power value or in the gradient of the Lyapunov exponent appears together with the opposite phase, the comparative determination means determines the range to be the predictive signal for falling asleep from the active state into the sleep state, is provided.

According to the present invention a the human condition evaluation system in which the comparative determination means includes a means for determining that the transition into the sleep state is made when each time-series change in the gradient of the power value or of the Lyapunov exponent appears at a low amplitude on the whole, after the sudden drop appears in the gradient of the power value or in the gradient of the Lyapunov exponent, is provided.

According to the present invention a the human condition evaluation system in which the bio-signal peak value detection means includes a means for carrying out differentiation for smoothing of the bio-signal data to identify a range in the vicinity of a differential waveform gradient at zero degrees to thereby detect the peak value from the original waveform corresponding to the range identified, is provided.

According to the present invention a human condition evaluation system in which the Lyapunov exponent peak value detection means includes a means for carrying out differentiation for smoothing of the Lyapunov exponent to identify a range in the vicinity of a differential waveform gradient at zero degrees to thereby detect the peak value from the original waveform corresponding to the range identified, is provided.

According to the present invention a human condition evaluation system in which the power value calculation means is a means for calculating, as a power value, a difference between an average peak value at the upper limit side and an average peak value at the lower limit side both in a certain time range of the bio-signal data, is provided.

According to the present invention a human condition evaluation system in which the gradient of the power value or the gradient of the Lyapunov exponent calculated by the gradient calculation means is a value obtained by a least-squares method, is provided.

According to the present invention a human condition evaluation system further composed of a means for performing frequency analysis on the gradient of the power value or the gradient of the Lyapunov exponent to determine a human condition, is provided.

According to the present invention a human condition evaluation system further composed of an output means for actuating an awakening means for awakening a person when the comparative determination means detects the predictive signal for falling asleep for the active state to the sleep state, is provided.

According to an alternate embodiment of the present invention , a computer program for letting a computer execute a process of evaluating a human condition by analyzing a bio-signal data detected by a bio-signal measurement instrument for measuring a bio-signal of a human, composed of a bio-signal peak value detection step for detecting a peak value for each cycle of an original waveform of the bio-signal data, a power value calculation step for calculating a difference between the peak value at an upper limit side and the peak value at a lower limit side for each prescribed time range using respective peak values obtained by the bio-signal peak value detection step to thereby set the difference as a power value, a gradient calculation step for obtaining a gradient of the power value with regard to time base in a certain time range by performing slide calculation a prescribed number of times at a prescribed overlap rate with regard to the prescribed time, and a comparative determination step for comparatively determining whether a sudden drop state of the gradient of the power value exists or not in time-series change in the gradient of the power value obtained by performing the slide calculation to thereby determine the time range in which the sudden drop state appears to be a predictive signal for falling asleep for an energy metabolism transition from the active state into the sleep state, is provided.

According to the present invention a computer program further composed of a Lyapunov exponent calculation step for calculating a Lyapunov exponent by performing chaos theory analysis on the bio-signal data, and a Lyapunov exponent peak value detection step for detecting a peak value for each cycle of a time-series change waveform of the Lyapunov exponent calculated by the Lyapunov exponent calculation means, in which the gradient calculation step includes a step for obtaining, in addition to the gradient of the power value, a gradient of respective peak values of the Lyapunov exponent with regard to time base in a certain time range obtained by the Lyapunov exponent peak value detection step, and in which the comparative determination step comparatively determines whether a sudden drop state exists or not in at least one of the time-series changes in the gradients of the power value and the Lyapunov exponent obtained by performing the slide calculation to determine a range in which the sudden drop state appears to be the predictive signal for falling asleep from the active state into the sleep state, is provided.

According to the present invention a computer program in which the comparative determination step compares the time-series changes in the gradients of the power value and the Lyapunov exponent which are obtained by performing the slide calculation with the gradient calculation means, and determines whether the gradients of the power value and the Lyapunov exponent are in opposite phases with each other or not before or in the range in which the sudden drop appears in the gradient of the power value or in the gradient of the Lyapunov exponent, and in the case where the sudden drop in the gradient of the power value or in the gradient of the Lyapunov exponent appears together with the opposite phase, the comparative determination step determines the range to be the predictive signal for falling asleep for the energy metabolism transition from the active state into the sleep state, is provided.

According to the present invention a computer program in which the comparative determination step includes a step for determining that the transition into the sleep state is made when each time-series change in the gradient of the power value or of the Lyapunov exponent appears at a low amplitude on the whole, after the sudden drop appears in the gradient of the power value or in the gradient of the Lyapunov exponent, is provided.

According to the present invention a computer program further composed of a step of performing frequency analysis on the gradient of the power value or the gradient of the Lyapunov exponent to determine the state of the human condition, is provided.

According to the present invention a computer program further composed of an output step for actuating an awakening means for awakening a person when the predictive signal for falling asleep for the active state to the sleep state is detected by the comparative determination step, is provided.

According to the present invention a computer-readable record medium in which a computer program is recorded, is provided.

BRIEF DESCRIPTION OF THE DRAWINGS

The foregoing and still other objects and advantages of the present invention will be more apparent from the following detailed explanation of the preferred embodiments of the invention in connection with the accompanying drawings.

FIGS. 4A to 4E are graphical charts showing the result of the frequency analysis on the gradient of the Lyapunov exponent in FIG. 2;

FIGS. 5A to 5E are graphical charts plotting a relation between frequency response of the gradient of the power value in FIGS. 3 and frequency with regard to a logarithm axis;

FIG. 6A to 6E are graphical charts plotting the relation between frequency response of the gradient of the Lyapunov exponent in FIG. 4 and frequency with regard to the logarithm axis;

FIGS. 8A to 8E are graphical charts showing the result of the frequency analysis on the gradient of the power value in FIG. 7;

FIGS. 9A to 9E are graphical charts showing the result of the frequency analysis on the gradient of the Lyapunov exponent in FIG. 7;

FIGS. 10A to 10E are graphical charts plotting the relation between frequency response of the gradient of the power value in FIG. 8 and frequency with regard to the logarithm axis;

FIGS. 11A to 11E are graphical charts plotting the relation between frequency response of the gradient of the Lyapunov exponent in FIG. 9 and frequency with regard to the logarithm axis;

FIGS. 13A to 13D are graphical charts showing the result of the frequency analysis on the gradient of the power value in FIG. 12;

FIGS. 14A to 14D are graphical charts showing the result of the frequency analysis on the gradient of the Lyapunov exponent in FIG. 12;

DETAILED DESCRIPTION OF THE INVENTIONS

Figure 1:
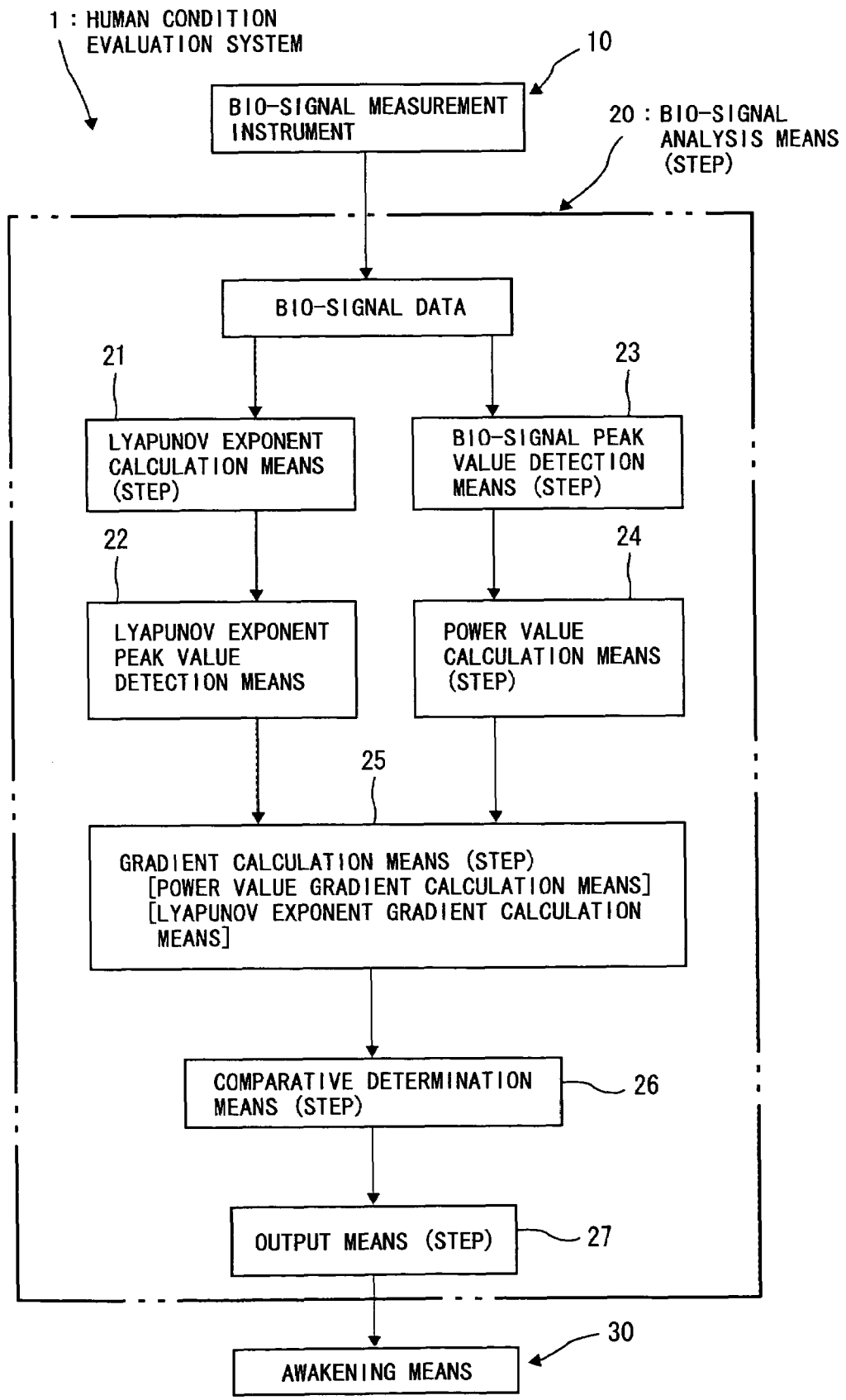
FIG. 1 is a block diagram showing a structure of a human condition evaluation system according to a first embodiment of the present invention.

Hereinafter, the present invention will be described in more detail based on embodiments shown in the drawings. FIG. 1 is a block diagram showing a human condition evaluation system according to an embodiment of the present invention. As shown in the drawing, a human condition evaluation system 1 of the present embodiment is composed of a bio-signal analysis means 20 for receiving a bio-signal data collected by a bio-signal measurement instrument 10.

As a bio-signal measurement instrument 10, one provided with a sensor such as a pressure sensor can be used. In the case of detecting a bio-signal of a person seated for example on a driver seat of a vehicle or a train, the pressure sensor can be used by being mounted on a seat back or a seat cushion of the driver seat, and in the case of detecting the bio-signal of a person on a bed with a body lying down, the pressure sensor can be used by being mounted on a cushioning layer of the bed. However, it is required not to give the person a feeling of something foreign, whereby a film-shaped piezoelectric element is preferably used as a pressure sensor by being affixed onto the seat back, the seat cushion, or a surface of the bed. This makes it possible with ease to detect, as a fluctuation of a pressure value, a vibration of a body surface caused together with a pulse being a bio-signal.

The bio-signal analysis means (step) 20 is composed of a Lyapunov exponent calculation means (Lyapunov exponent calculation step) 21, a Lyapunov exponent peak value detection means (Lyapunov exponent peak value detection step) 22, a bio-signal peak value detection means (bio-signal peak value detection step) 23, a power value calculation means (power value calculation step) 24, a gradient calculation means (gradient calculation step) 25, and a comparative determination means (comparative determination step) 26.

A Lyapunov exponent is one of chaos indicators and is a value indicating, as an indicator, a dependence degree of the chaos on the initial value, that is, an amount representing a divergence degree, in accordance with elapse of time, of neighboring two trajectories among trajectories drawn by attractors. Specifically, the bio-signal data collected by the bio-signal measurement instrument 10 is embedded by the Lyapunov exponent calculation means (Lyapunov exponent calculation step) 21 for example at an embedded delay time of 25 msec in fourth dimension to generate an attractor. With an evolution time, which equals to the embedded delay time, being given, the Lyapunov exponent is calculated. Incidentally, for generating the attractor in a fourth-dimension phase space, at least 20000 pieces of time-series bio-signal data are required. For calculating the Lyapunov exponent, there are a Wolf method, a Kantz method, and the like, whereas, in the case of determining a human condition or the like of a driver, immediate calculation is important, otherwise a feedback of resultant evaluation may sometimes lose meanings. Therefore, it is preferable to use the approximate calculation of a Sano-Sawada method to practically perform a real-time processing.

The Lyapunov exponent peak value detection means (Lyapunov exponent peak value detection step) 22 of the present embodiment detects a peak value for each cycle of the time-series change waveform of the Lyapunov exponent to be calculated as described above. Specifically, the peak value differentiates for smoothing the Lyapunov exponent to be calculated as described above to identify a range in the vicinity of a differential waveform gradient at zero degrees, and detection is carried out from original waveforms of time-series change in the Lyapunov exponent corresponding to the identified range. Incidentally, as for peak values, even though there are the peak value at the upper limit side and that at the lower limit side for each cycle, in this embodiment, only the peak value at the upper limit side is detected and adopted in the gradient calculation means described later.

The bio-signal peak value detection means (bio-signal peak value detection step) 23 detects the peak value for each cycle of the original waveform of the bio-signal data obtained by the bio-signal measurement instrument 10. Specifically, similarly as in the case of detecting the peak value of the Lyapunov exponent described above, the bio-signal data is differentiated for smoothing to identify the range in the vicinity of a differential waveform gradient at zero degrees, and then the peak value is detected from among the original waveforms of the bio-signal data corresponding to the identified range.

The power value calculation means (power value calculation step) 24 divides the peak value for each cycle of original waveform of the bio-signal data obtained by the bio-signal peak value detection means 23 into those for every preset time range, for example, those for every five seconds, and a difference between an averaged upper limit side peak value and an averaged lower limit side peak value is calculated as a power value within the time range. However, for highlighting a change amount, in this embodiment, a square value of the difference between the averaged peak value at the upper limit side and the averaged peak value at the lower limit side in a certain time range is defined as a power value. The power value means a resistance value of the living body against intrusion and destruction from outside.

The gradient calculation means (gradient calculation step) 25 calculates the gradient of each peak value of the Lyapunov exponent in a certain time range with regard to time base obtained by the Lyapunov exponent peak value detection means 22 and the gradient of the power value in a certain time range with regard to time base obtained by the power value calculation means 24 by performing slide calculation a prescribed number of times at a prescribed overlap rate with regard to the prescribed time. The slide calculation is made as described below.

For instance, for calculating a gradient for T second (s) at a slide overlap rate of 90%, first, the peak value of the Lyapunov exponent for 0 (s) to T (s) and the gradient of the power value with regard to time base is found by a least-squares method. Next, the gradient for the following time frame is calculated by the least-squares method.

$T/10(s) \sim T+T/10(s)$  slide calculation (1)

$2 \times T/10(s) \sim T+2 \times T/10(s)$  slide calculation (2)

$n \times T/10(s) \sim T+n \times T/10(s)$  slide calculation ($n$)

The gradient of the peak value of the Lyapunov exponent and the gradient of the power value thus obtained represent a state of energy control system and a state of energy supply system respectively, as mentioned before. Accordingly, when any of them shows a large drop in time-series change, a transition from a drowsy fatigue state through a rest state to a sleep state can be detected, the drowsy state being caused due to lowering functional status of an energy generation system, which is a functioning state of muscle, triggered by functional status of the energy control system or the energy supply system, as a cause. Beyond that, as described above, in the present embodiment, monitoring is performed not for the bio-signal and the original waveform of the Lyapunov exponent but for respective gradients obtained by performing slide calculation which further enlarge the time-series change in functioning status of the energy control system and the energy supply system of the living body, so that delicate conditions thereof can be understood precisely.

The comparative determination means (comparative determination step) 26 is a program for comparatively determining whether the gradient of the power value shows a sudden drop or not, or for the case in which both the gradients of the power value and the Lyapunov exponent are obtained as in this embodiment, whether a state that any one of the gradient of the power value or the gradient of the Lyapunov exponent shows a sudden drop or not, by using the gradient of the power value and the gradient of the peak value of the Lyapunov exponent which are obtained by the gradient calculation means 25, to thereby determine the range having the sudden drop to be a predictive signal for falling asleep from an active state to the sleep state.

The comparative determination means 26 can be structured to detect the predictive signal for falling asleep only by the sudden drop in the gradient of the power value or of the Lyapunov exponent obtained by the gradient calculation means 25, however, as can be found from an test example described later, when the gradient of the power value and the gradient of the Lyapunov exponent are shown in the same graph by overlapping with each other and when the transition from the active state to the sleep state is made, in a range just before any sudden drop, the gradient of the power value and the gradient of the Lyapunov exponent are in opposite phases. Therefore, a mere sudden drop in any gradient without adjacent opposite phase can be determined to be incomplete sleep state being doze state. Accordingly, the comparative determination means 26 can be preferably structured to determine as the predictive signal for falling asleep from the active state into the sleep state when the sudden drop appears together with the opposite phases.

In addition, when the gradient of the power value and the gradient of the Lyapunov exponent are shown in the same graph by overlapping with each other, after the sudden drop in the gradient of the power value or of the gradient of the Lyapunov exponent, each time-series change in gradient of the power value or the gradient of the Lyapunov exponent sometimes appears at a low amplitude on the whole, and when there is no such a region at a low amplitude, complete transition into the sleep state is not made in some cases. Hence, a structure, in which determination of transition into the sleep state is made only when such a region at a low amplitude appears after the sudden drop together with the opposite phases, is also acceptable.

The sudden drop in one of the gradients of the power value and the Lyapunov exponent can not always be defined as the transition from the active state into a complete sleep state, but be defined at least as a state of fatigue with drowsiness. Consequently, when determining the predictive signal for falling asleep, it is optional to take the opposite phase or the region at a low amplitude into consideration or not, in addition to the sudden drop, and combination of such a determination base can be set properly depending on the usage of the human condition evaluation system of the present invention, provided that an appearance of such a sudden drop is determined to be the predictive signal for falling asleep in principle. However, in the case of using the system for detecting drowsiness of the driver to output a signal via an output means (output step) 27 as an electronic signal, and using in combination with an awakening means 30 such as a safety alarm, it is important to recover wakefulness as quick as possible. Therefore, in this case, when any gradient of the power value or the Lyapunov exponent shows the sudden drop, it is preferable to determine the sudden drop range to be the predictive signal for falling asleep, before fully fallen asleep, to thereby output to the awakening means 30.

It can be further structured to perform frequency analysis on the gradients of the power value and the Lyapunov exponent which are calculated by the gradient calculation means 25, and determine the transition into the sleep state, depending on whether or not frequency response area is decreased, by the comparative determination means 26. Similarly, still another structure is acceptable, in which a determination whether-or not a fluctuation calculated based on the result of the frequency analysis approximates the 1/f fluctuation enables to determine whether or not the human condition is near to the sleep state in view of metabolism.

These can be optionally combined into the human condition evaluation system of the present invention depending on usage of the system, as mentioned before. For instance, when the system is used for a sleep test or the like, these components are preferably added for more accurate detection of the human condition. Meanwhile, when the system is used for alarming the driver or the like, if the awakening means 30 is structured to start operation after receiving the results of these calculations of frequency analysis or the like, alarm timing is generally delayed, since these calculations of frequency analysis or the like are made after the calculation of the gradients of the power value and the Lyapunov exponent. Nevertheless, concurrent output is still possible. For instance, depending on the program, the frequency analysis or the like can be processed essentially in parallel with the gradient calculation by the gradient calculation means 25 for immediate output, making it possible to determine in consideration also of the result of the frequency analysis or the like to thereby make the awakening means 30 start operation.

TEST EXAMPLE

Subsequently, an experimental sleep test is conducted to calculate the time-series changes in the gradient of the power value (Power gradient) and the gradient of the peak value of the Lyapunov exponent (Lyapunov exponent gradient). Further, frequency analysis is conducted on the gradient of the power value and the gradient of the peak value of the Lyapunov exponent during sleep and during rest. Note that a pressure sensor composed of a film-shaped piezoelectric element (product name: PIEZO FILM LDT series, model number: LDT4-028K/L, by Tokyo Sensor Co., Ltd.) is used as a bio-signal measurement instrument in both the tests, and is set under a mat (futon) or a haunch part of a seat which support a subject for collecting bio-signals. The calculations of the Power gradient and the Lyapunov exponent gradient are made after obtaining the peak values of the collected bio-signal data and the Lyapunov exponent for every 5 seconds over the whole measurement time. In the gradient calculating means, the slide overlap rate is set at 90%, and a first gradient calculation is made for first three minutes after starting measurement. That is, firstly, respective gradients are calculated for a time range of 0 to 180 seconds after starting measurement, secondly, respective gradients are calculated for the time range of 18 to 198 seconds after starting measurement, thirdly, respective gradients are calculated for the time range of 36 to 216 seconds after starting measurement, and, for the calculation, this procedure is repeated until the measurement time comes to an end. The calculation results are plotted with regard to the time measured, respectively.

Test Example 1

Subject: A (sex: male, age: 61, height: 163 cm, weight: 63 kg, health condition: fine)

Figure 2:
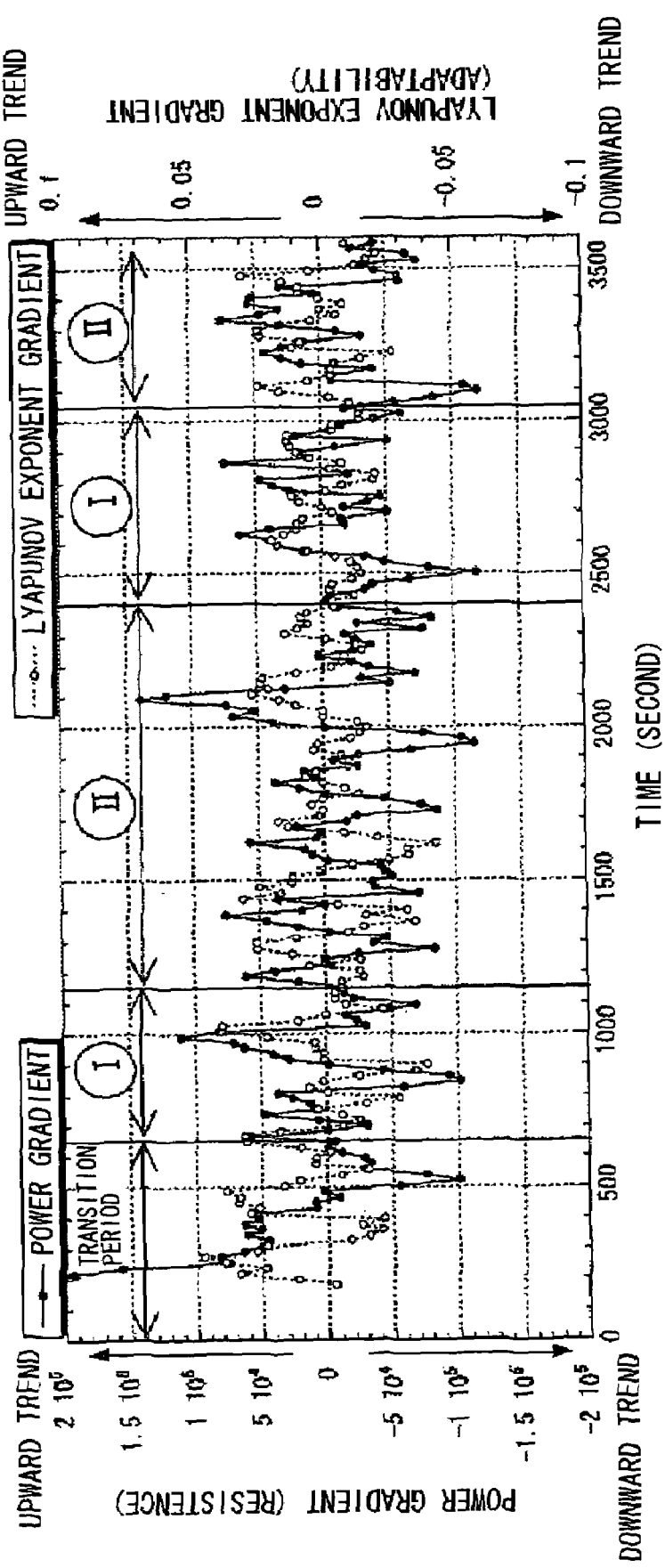
FIG. 2 is a graphical chart showing a gradient of a power value and a gradient of a Lyapunov exponent in test example 1.
Figure 3A:
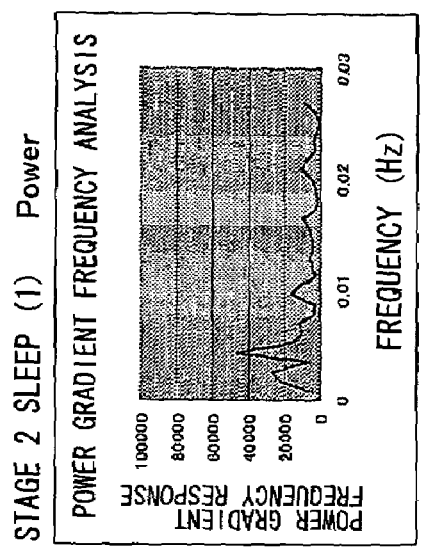
FIGS. 3A to 3B are graphical charts showing a result of a frequency analysis on the gradient of the power value in FIG. 2.
Figure 3B:
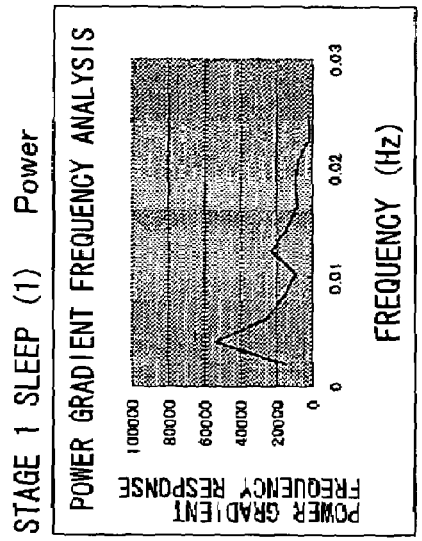
Figure 3C:
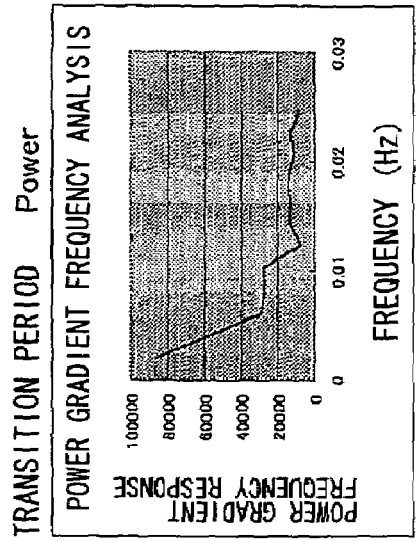
Figure 3D:
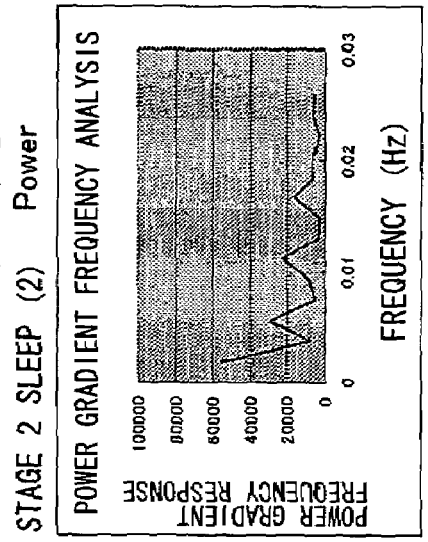
Figure 3E:
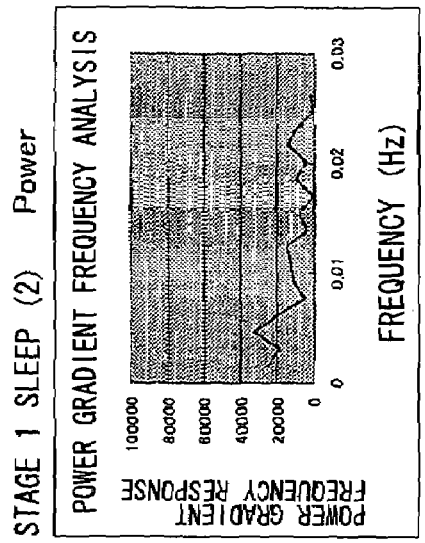

Experimental Conditions:
Measurement time: 1 hour, start at 13:22
Subject supporting member: mat made from cotton
Posture during measurement: lies on his back Result:
FIG. 2 shows a Power gradient and a Lyapunov exponent gradient of test example 1.
(1) Comment (Self-assessment by the Subject)
The subject feels to be in a deep sleep after 7 to 8 minutes later after staring measurement to the end of the test. The subject wakes up to have a feeling of renewed and regained vitality.
(2) Considerations
Due to his posture of lying on his back, the Power gradient starts to decline after the start of the test, and after the decline trend slows down, the Power gradient shows a large decline around 420 to 520 seconds later after the start, and the gradient shows upward trend thereafter. The upward trend of the Power gradient can be deemed as a defensive physical energy increase for sustaining life and maintaining health as a result of transition into the sleep state. The transition from the active state (rest state) into the sleep state (metabolism in rest into metabolism in sleep) is deemed to be made in the vicinity of the first large decline in the Power gradient. Similarly, the Lyapunov exponent gradient shows a decline around 500 to 550 seconds later after the start, and at the same time, brain activity governing the energy control system makes the transition into the sleep state.

In the sleep state after the rest state through the transition period into sleep, the Power gradient moves in order of stage 1 sleep, stage 2 sleep, stage 1 sleep, and stage 2 sleep, indicating a typical sleep pattern of an aged people, and the test ends and the subject A is woken up at the stage 2 sleep. When people awake at the stage 2 sleep, it is said that most people feel refreshed on awakening, ensuring the comment by the subject A. For reference, the transition period in view of sleep (emerging period of the predictive signal for falling asleep) is a drowsy state, the stage 1 sleep is a light sleep state in a border between a wakeful state and the sleep state and after the transition period (a level in which the Power gradient and the Lyapunov exponent gradient move essentially in the same phase), and the stage 2 sleep is a state not to respond to external stimulation (a level in which the Power gradient and the Lyapunov exponent gradient move in opposite phases each other relatively frequently). In other words, a state in which muscles are relaxed, blainstem stimulation is lightened, and a sleep is induced.

FIGS. 3A to 3E are graphic charts showing results of frequency analysis on the Power gradient in FIG. 2, and FIGS. 4A to 4E are graphic charts showing results of frequency analysis on the Lyapunov exponent gradient. As is obvious by the results, in frequency response during the transition period into sleep in FIGS. 3A and FIG. 4A, there is a frequency zone which largely projects as compared with the other states, indicating a characteristic in the frequency analysis.

That is, as proven in FIGS. 3A to 3E and FIGS. 4A to 4E, the subject apparently made the transition into the sleep state after around 420 to 520 seconds from the start of the test, during which the Power gradient had shown a large drop as shown in FIG. 2.

FIG. 5 is a graphical chart plotting a relation between frequency response of the Power gradient and frequency with regard to a logarithm axis based on the analysis in FIG. 3, and FIG. 6 is a graphical chart plotting a relation between frequency response of the Lyapunov exponent gradient and frequency with regard to the logarithm axis based on the analysis in FIG. 4. As shown in these drawings, it is found that in the stage 1 sleep in FIG. 5B and FIG. 6B, gradients β are large, and a response to external stimulation can be seen, whereas, in the transition period into sleep in FIG. 5A and FIG. 6A, any gradients β are smaller than that of the stage 1 sleep, in which the subject consumes low calories, is stabilized psychologically, and is dropping off to a sleep.

According to the result, a range around 200 to 520 seconds in FIG. 2 showing a large drop in the Power gradient corresponds to the predictive signal for falling asleep for the subject of this test example. Specifically, the state in which a sudden drop in the Power gradient is shown is a time when a person feels drowsiness just before completely making transition into sleep. Accordingly, when the comparative determination means 26 detects such a drop in the Power gradient, it is possible to make the driver recover the wakeful state by outputting, as an electronic signal, the detected signal via an output means 27 to the awakening means 30 such as an alarm horn generating device if for instance it is installed in a vehicle, thereby making the awakening means 30 start operation. As a result, it is also possible to make a signal which induces the driver to take a rest in a neighborhood parking area.

Test Example 2

Subject: B (sex: male, age: 31, height: 161 cm, weight: 59 kg, health condition: fine)

Figure 7:
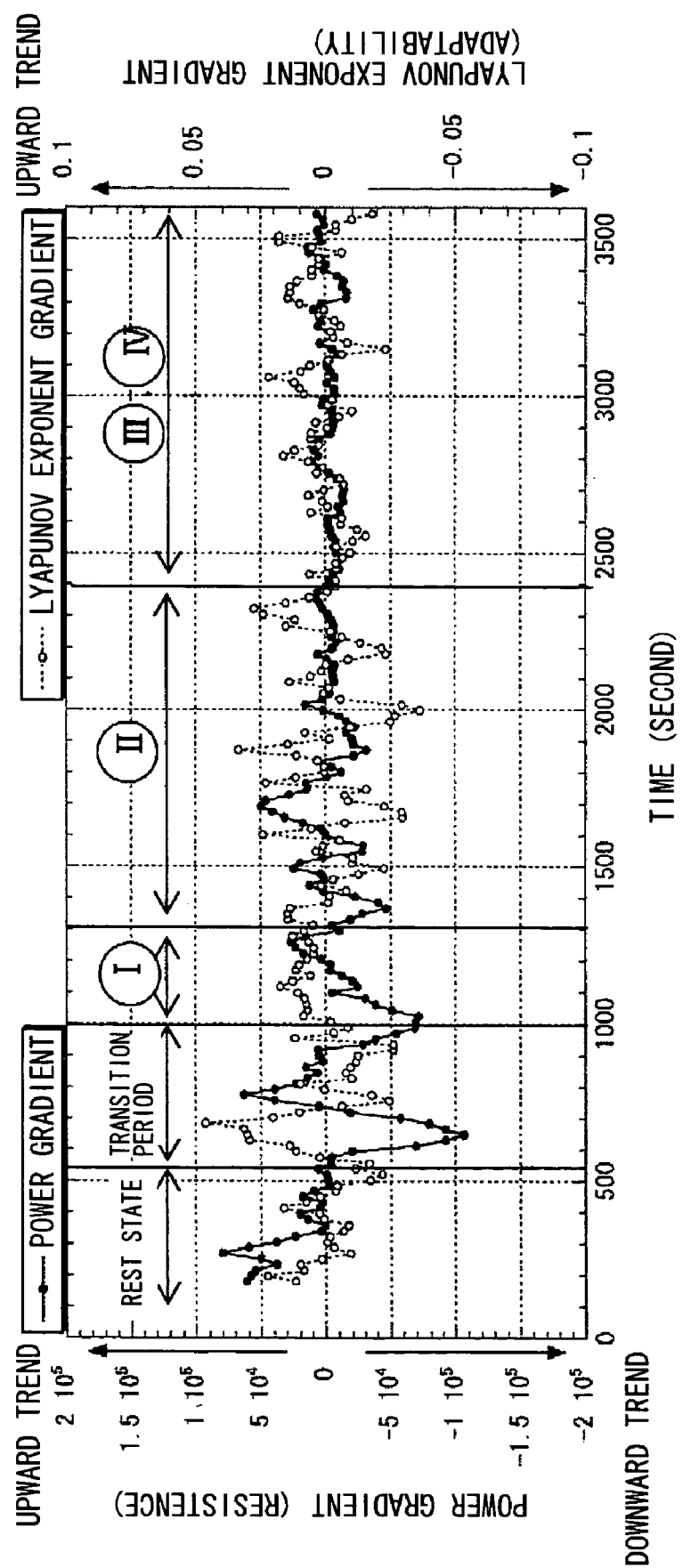
FIG. 7 is a graphical chart showing the gradient of the power value and the gradient of the Lyapunov exponent in test example 2.

Experimental Conditions:
Measurement time: 1 hour, start at 00:45
Subject supporting member: futon made from feather
Posture during measurement: lies on his back Result:
FIG. 7 shows a Power gradient and a Lyapunov exponent gradient of test example 2. FIGS. 8A to 8E are graphic charts showing a result of frequency analysis on the Power gradient in FIG. 7, FIGS. 9A to 9E are graphic charts showing a result of frequency analysis on the Lyapunov exponent gradient, and FIGS. 10A to 10E and FIGS. 11A to 11E are graphic charts showing a relation between the Power gradient frequency response and frequency plotted with regard to the logarithm axis, respectively.
(1) Comment (Self-assessment by the Subject)
Although subject fails to fall into a deep sleep since estimated 15 minutes later after staring measurement, he has a muzzy head for a while when he wakes up.
(2) Considerations
As shown in FIG. 7, when around 450 to 550 seconds passed after the start of the test, the Power gradient shows a large drop, and turns upward thereafter, whereas, suddenly drops again around 650 to 1050 seconds after the start of the test. At the time of the first large drop in the Power gradient, the subject is considered to feel drowsy. In the range of the second drop in the Power gradient, the Lyapunov exponent gradient drops together, while in the range of the first drop in the Power gradient, the Lyapunov exponent gradient goes up to be in opposite phase with the Power gradient. This is a resistance to the transition into sleep. After the second drop and up, both the Power gradient and the Lyapunov exponent gradient stay at a low amplitude.

With these points considered together with the self-assessment comment by the subject, in the range showing the first drop in the Power gradient, which is in opposite phase with the Lyapunv exponent gradient, the subject is considered to start to feel drowsy, and in the range showing the second drop in the Power gradient and a drop in the Lyapunov exponent gradient, which is in the same phase with regard to Lyapunv exponent gradient, the subject is considered to be in border between the wakeful state and the sleep state, being the stage 1 sleep. The subject is considered to make the transition into the stage 2 sleep during around 1300 to 2300 seconds later, and be in stage 3 sleep and stage 4 sleep after around 2300 seconds later. Note that the stage 3 sleep and the stage 4 sleep are deep sleeps and referred to as slow-wave sleeps. In the Power gradient and Lyapunv exponent gradient, it is a state where the amplitude is at a low level on the whole as compared with the amplitude in the stage 1 sleep and the stage 2 sleep.

That is, the transition into the sleep state is made after the following wave forms appear in series: (1) a waveform indicating that the Power gradient and the Lyapunov exponent gradient are in opposite phases, being a resistance against the transition into sleep, (2) a waveform indicating the sudden drop in the Power gradient, and (3) at least one of the waveforms of the Power gradient and the Lyapunov exponent gradient at a low amplitude appearing after the sudden drop. Therefore, when these three states are taken into consideration for determining the predictive signal for falling asleep, the detection of the transition into sleep can be made most surely. Incidentally, these three states appear prominently in test example 2, though, the same pattern is indicated also in test example 1. In test example 1, at a time just before the range around 420 to 520 seconds in which the Power gradient drops suddenly, the Power gradient and the Lyapunov exponent gradient are essentially in opposite phases, and just after the sudden drop, both the Power gradient and the Lyapunov exponent gradient are at a low amplitude, as a trend.

Of the three states described above, both of the waveform indicating the opposite phase and the waveform indicating the sudden drop in the Power gradient are auras of the complete sleep state. Therefore, when the present invention is used for evaluating a human condition for example of a driver, preferably, it is structured so that at least one of the waveforms indicating the opposite phase and the sudden drop in the Power gradient is determined to be the predictive signal for falling asleep, if they appear, and that the signal is outputted via the output means 27 to the awakening means 30.

According to the result of the frequency analyses on the Power gradient and the Lyapunov exponent gradient shown in FIGS. 8 and FIGS. 9, it is found that frequency response areas during sleep are smaller than that of the transition period into sleep (introduction period into sleep), and that a distinctive frequency response can be seen in the transition period into sleep, in every case. On the back of these, it is ensured that the transition in metabolism is made from the rest state into the sleep state before and after the time zone determined to be the predictive signal for falling asleep stated above. The frequency response area of the stage 3 sleep is smaller than that of the stage 2 sleep, and that of the stage 2 sleep is smaller than that of the stage 1 sleep. It is therefore found that the stage 3 sleep is more profound than the stage 1 sleep. According to the calculation result of a fluctuation in frequency response shown in FIGS. 10 and FIGS. 11, similarly to test example 1, a gradient β in the stage 1 sleep is large, in which a response to external stimulation is indicated, whereas, the gradient β in the transition period into sleep is smaller than that of the stage 1 sleep, in every case, in which it is ensured that the subject consumes low calories, is stabilized psychologically, and is dropping off to a sleep.

Test Example 3

Subject: C (sex: male, age: 31, height: 166 cm, weight: 70 kg, health condition: fine)

Figure 12:
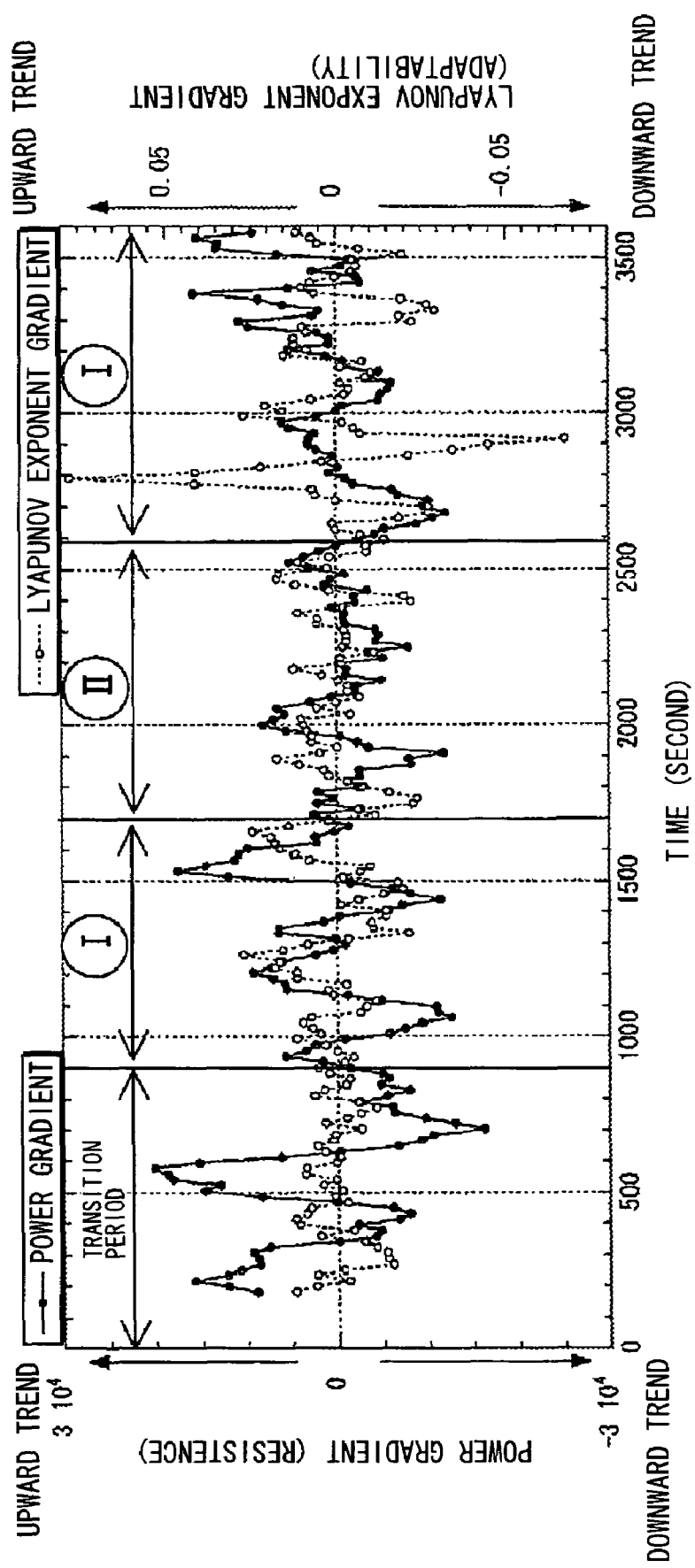
FIG. 12 is a graphical chart showing the gradient of the power value and the gradient of the Lyapunov exponent in test example 3.
Figure 15A:
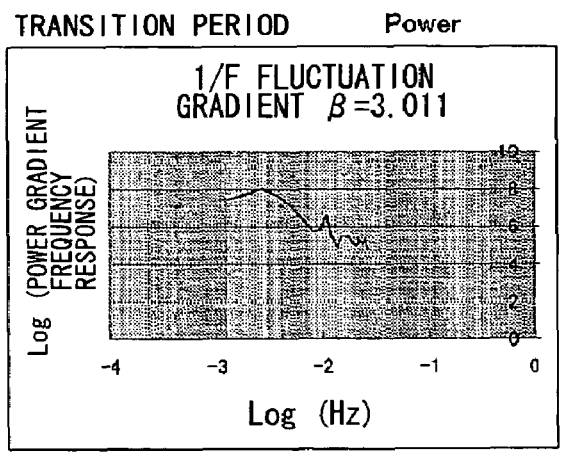
FIGS. 15A to 15D are graphical charts plotting the relation between frequency response of the gradient of the power value in FIG. 13 and frequency with regard to the logarithm axis.
Figure 15B:
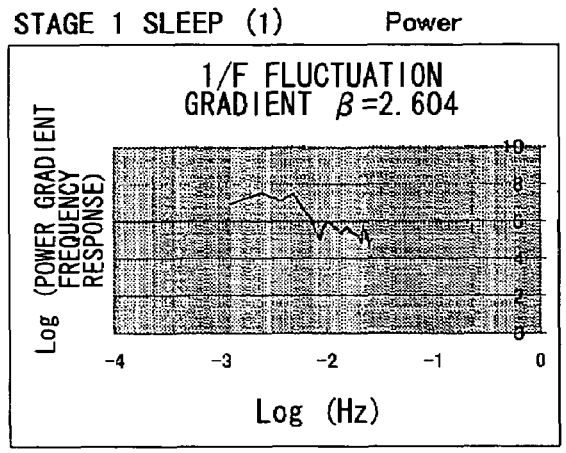
Figure 15C:
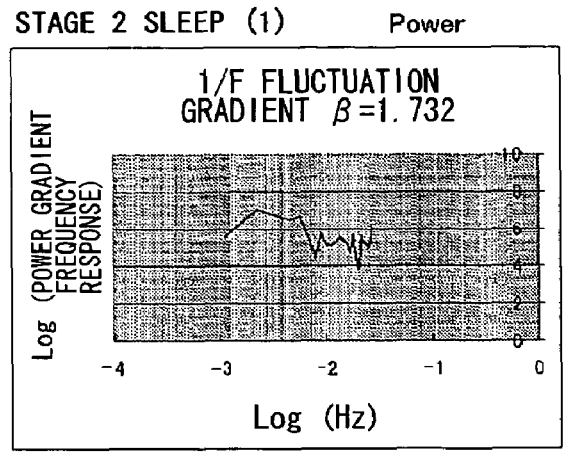
Figure 15D:
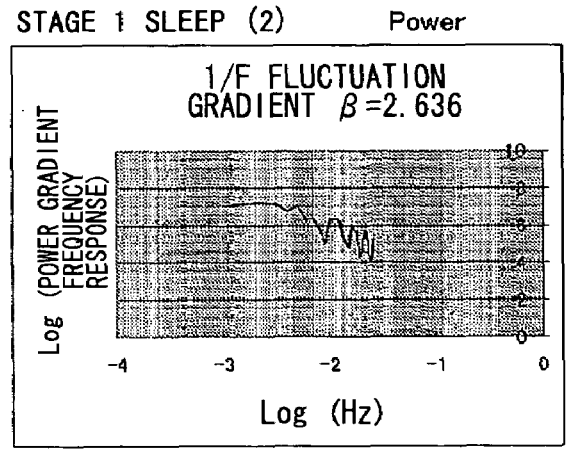
Figure 16A:
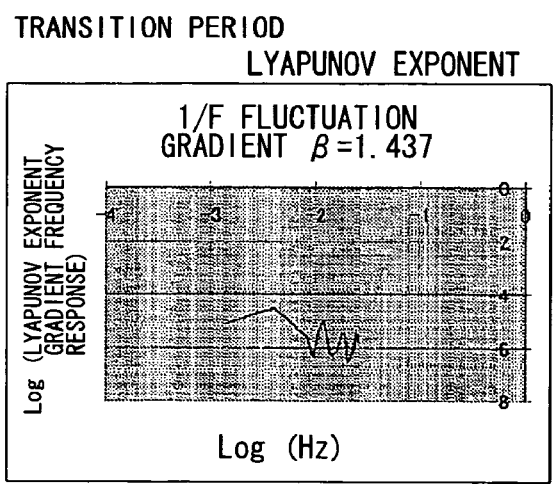
FIGS. 16A to 16D are graphical charts plotting the relation between frequency response of the gradient of the Lyapunov exponent in FIGS. 14 and frequency with regard to the logarithm axis.
Figure 16B:
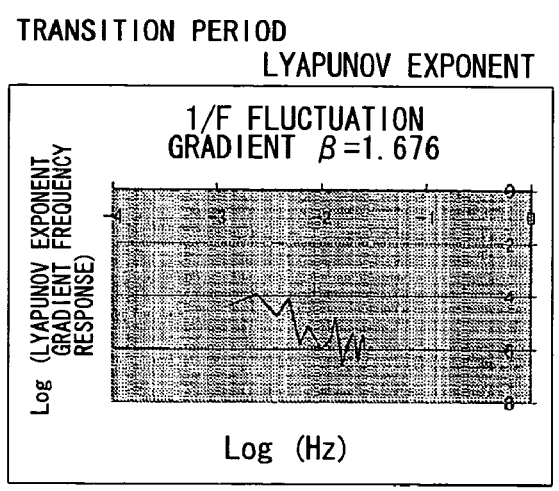
Figure 16C:
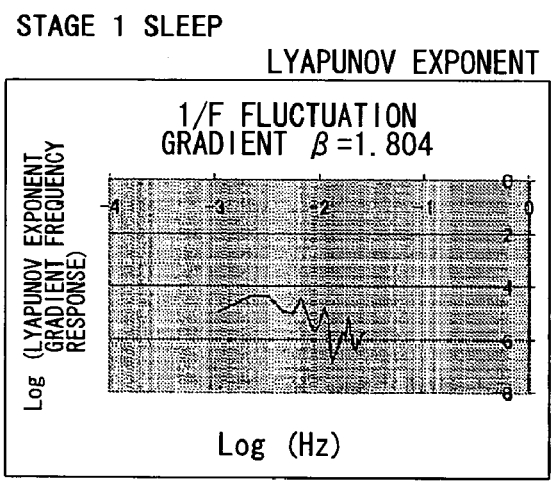
Figure 16D:
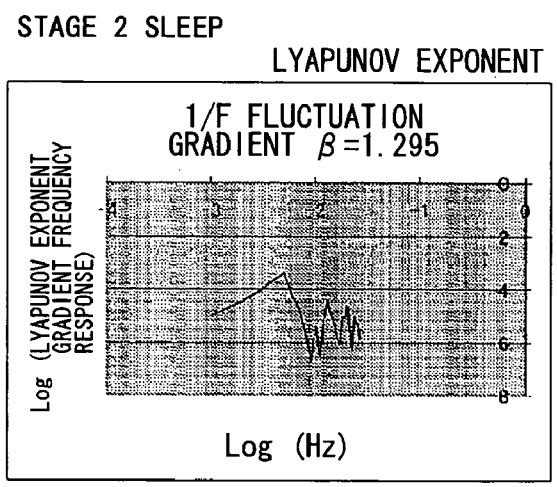

Experimental conditions:
  Measurement time: 1 hour, start at 14:30
  Subject supporting member: mat made from cotton
  Posture during measurement: lies on his back Result:
FIG. 12 shows a Power gradient and a Lyapunov exponent gradient of test example 3. FIGS. 13A to 13D are graphic charts showing a result of frequency analysis on the Power gradient in FIG. 12, FIGS. 14A to 14D are graphic charts showing a result of frequency analysis on the Lyapunov exponent gradient, and FIGS. 15A to 15D and FIGS. 16A to 16D are graphic charts showing a relation between a Power gradient frequency response and frequency, and a Lyapunov exponent gradient frequency response and frequency, both plotted with regard to the logarithm axis, respectively.

(1) Comment (Self-assessment by the Subject)

The subject has a feeling that he has a sleep for about 20 minutes after 20 minutes later the start of the test, whereas, he is hard to say whether he stays awake or in sleep thereafter.

(2) Considerations

As is clear also from the comment by the subject, the subject of this test example is deemed to travel between the wakeful state and the sleep state by staying in the stage 1 sleep being a drowsy state without dropping into a deep sleep from start to end in the test. As is obvious in FIG. 12, the Power gradient suddenly drops twice during 700 seconds from the start of the test, and the period is deemed to be the transition period into sleep. However, thereafter, the subject experiences the stage 1 sleep for around 900 to 1700 seconds, the stage 2 sleep, which has smaller ups and downs, for around 1700 to 2600 seconds, and again the stage 1 sleep to the end of the test. In the meantime, the Lyapunov exponent gradient declines for around 300 seconds from just after the start of the test, once goes up thereafter, and moves to a state of a slightly low amplitude.

Therefore, the stage 2 sleep in which response to external stimulation slows down corresponds to the time range that the subject feels to have a sleep. Besides, there are large ups and downs after 2500 seconds from the start in the Lyapunov exponent gradient, indicating a response to external stimulation, where brain does not sleep completely. This point also agrees with the comment by the subject.

It is understood from the result of frequency analysis on the Power gradient and the Lyapunov exponent gradient shown in FIG. 13 and FIG. 14 that the drop especially in frequency response area of the Power gradient is more obvious during sleep than during the transition period into sleep, revealing a characteristic frequency response in the transition period into sleep. It is thereby ensured that the transition from the rest state to the sleep state is made before and after the time range determined to be the predictive signal for falling-asleep mentioned before. Also, from the result of a fluctuation calculation of the frequency response shown in FIG. 15 and FIG. 16, it is found that, particularly in the Lyapunov exponent, the gradient β in the stage 1 sleep is larger and indicating a response to external stimulation, while the gradients β in the transition period into sleep are smaller than the gradient β in the stage 1 sleep, indicating that the subject is psychologically stabilized and is in the course of the transition into sleep.

Figure 17:
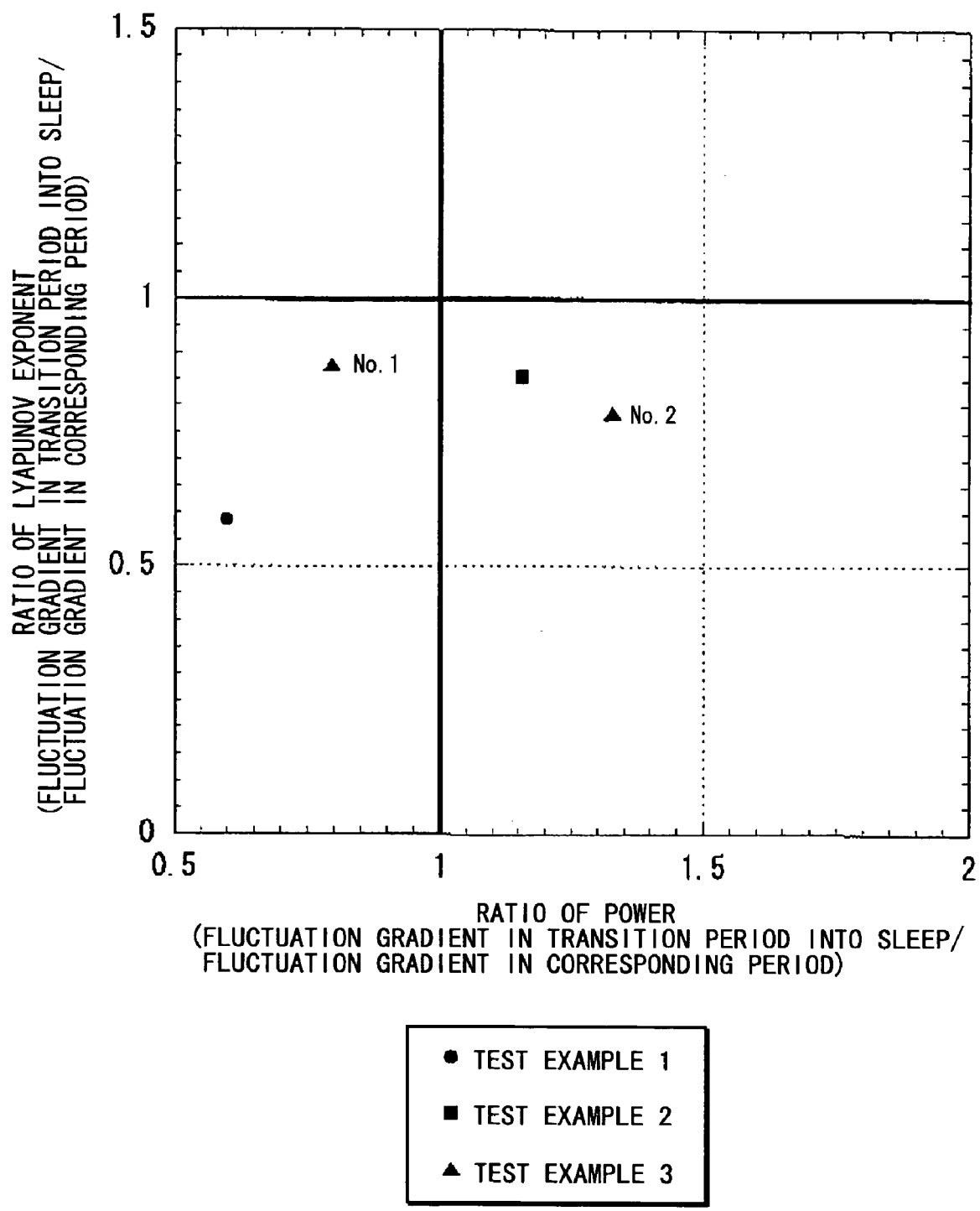
FIG. 17 is a graphical chart showing a ratio of a fluctuation gradient during a transition period into sleep to that of an applicable zone for each test example.

With an aim to clarify a view on the fluctuation gradient β in test example 1 and test example 3, a ratio of the fluctuation gradient β in the transition period into sleep to that of the stage 1 sleep being just after the transition period into sleep is calculated, and in test example 2, a ratio of the fluctuation gradient β in the transition period into sleep to that of the stage 1 sleep (No. 1) being just after the transition period into sleep, and a ratio of the fluctuation gradient β in the transition period into sleep to that of the rest state being just before the transition period into sleep are calculated respectively and are plotted in FIG. 17. It is obvious from the result that psychological stabilization is enhanced in the transition period into sleep in which the ratio is 1 or below for the Lyapunov exponent, while for the power value, the ratio is 1 or below, or slightly over 1, in which consumption of calorie falls and the transition is in progress.

In the embodiment described hereinabove, the analysis on the Lyapunov exponent and the analysis on the power value are employed concurrently. As a result, by detecting the sudden-drop range or the like in one of the Lyapunov exponent gradient and the Power gradient, it is possible to detect the predictive signal for falling asleep stably without regard to individual differences, health conditions, and the like. Meanwhile, the detection of the sudden-drop range or the like by focusing simply on the power value gradient also allows the detection of the predictive signal for falling asleep essentially, as is obvious from the above-described test examples, so that a technique focusing simply on the power value is even possible to provide a novel human condition evaluation system different from the conventional human condition evaluation system depending simply on the Lyapunov exponent.

Incidentally, the bio-signal analysis means (bio-signal analysis step), which is a computer program, composed of the Lyapunov exponent calculation means (Lyapunov exponent calculation step), the Lyapunov exponent peak value detection means (Lyapunov exponent peak value detection step), the bio-signal peak value detection means (bio-signal peak value detection step), the power value calculation means (power value calculation step), the gradient calculation means (gradient calculation step), the comparative determination means (comparative determination step), and so forth, can be provided by being recorded in a record medium. The "record medium" is a medium capable of holing and supporting a program which itself is impossible to occupy a space, such as a flexible disc, a hard disc, a CD-ROM, a MO (magneto-optical disc), a DVD-ROM, and the like. Also, it is possible to transmit the program according to the present invention from a computer in which the program is installed to the other computer via a communications line. Further, it is surely possible to form the human condition evaluation system of the present invention by way of pre-install or download of the program into a general-purpose terminal equipment.

The present invention is structured that a bio-signal analysis means includes a bio-signal peak value detection means for detecting a peak value for each cycle of an original waveform of a bio-signal data, and a power value calculation means for calculating a difference between the peak value at an upper limit side and the peak value at a lower limit side for every prescribed time range using respective peak values obtained by the bio-signal peak value detection means to thereby set the difference as a power value so that a predictive signal for falling asleep at a time when metabolism changes from an active state into a sleep state in a living body can be determined based on a time-series change in the power value. Therefore, according to the present invention, differently from the conventional human condition evaluation using a Lyapunov exponent as an indicator, a novel human condition evaluation system focusing attention on an energy generation system of a living body can be provided.

Further, in the present invention, there is provided a gradient calculation means for obtaining gradient(s) of the power value and/or the Lyapunov exponent with regard to time base in a certain time range by performing slide calculation a prescribed number of times at a prescribed overlap rate with regard to the prescribed time, which allows accurate and real-time determination of the time-series change(s) in the power value and/or the Lyapunov exponent more than ever, so that the transition from the active state into the sleep state can be detected accurately.

Furthermore, as a bio-signal analysis means, by adopting a means employing the Lyapunov exponent of the bio-signal together with the power value, more accurate determination can be made without regard to individual differences and/or health conditions.

What is claimed is:

1. A human condition evaluation system comprising:
   a bio-signal measurement instrument effective to measure a bio-signal of a human and to gather bio-signal data based on said measurements,
   a bio-signal analyzer effective said bio-signal data;
   wherein said bio-signal analyzer includes;
   a bio-signal peak value detector effective to detect a maximum and minimum peak value for each cycle of an original waveform of the bio-signal data,
   a power value calculator effective to calculate a difference between the maximum peak value of said waveform and the minimum peak value of said waveform for each prescribed time range using respective peak values obtained by said bio-signal peak value detector to thereby set the difference as a power value,
   a gradient calculator effective to obtain a gradient of the power value with regard to time base in a certain time range by performing slide calculation a prescribed number of times at a prescribed overlap rate with regard to the prescribed time, and
   a comparative determinator effective to comparatively determine whether a sudden drop state of the gradient of the power value exists or not in time-series change in gradient of the power value obtained by performing the slide calculation to thereby determine the time range in which the sudden drop state appears to be a predictive signal for falling asleep from an active state into a sleep state.

2. The human condition evaluation system according to claim 1, wherein said bio-signal analyzer includes a Lyapunov exponent calculator effective to calculate a Lyapunov exponent by performing chaos theory analysis on the bio-signal data, and a Lyapunov exponent peak value detector effective to detect a peak value for each cycle of a time-series change waveform of the Lyapunov exponent calculated by said Lyapunov exponent calculator, wherein said gradient calculator includes a means for obtaining, in addition to of the power value, a gradient of respective peak values of the Lyapunov exponent with regard to time base in a certain time range obtained by said Lyapunov exponent peak value detector, and wherein said comparative determinator comparatively determines whether a sudden drop state exists or not in at least one of the time-series changes in the gradients of the power value and the Lyapunov exponent obtained by performing the slide calculation to determine a range in which the sudden drop state appears to be the predictive signal for falling asleep from the active state into the sleep state.

3. The human condition evaluation system according to claim 2, wherein said comparative determinator compares the time-series changes in the gradients of the power value and the Lyapunov exponent which are obtained by performing the slide calculation with said gradient calculation means, and determines whether the gradients of the power value and the Lyapunov exponent are in opposite phases with each other or not before or in the range in which the sudden drop appears in the gradient of the power value or in the gradient of the Lyapunov exponent, and in the case where the sudden drop in the gradient of the power value or in the gradient of the Lyapunov exponent appears together with the opposite phase, said comparative determinator determines the range to be the predictive signal for falling asleep from the active state into the sleep state.

4. The human condition evaluation system according to claim 1, wherein said comparative determinator is further effective to determine that the transition into the sleep state is made when each time-series change in the gradient of the power value or of the Lyapunov exponent appears at a low amplitude on the whole, after the sudden drop appears in the gradient of the power value or in the gradient of the Lyapunov exponent.

5. The human condition evaluation system according to claim 1, wherein said bio-signal peak value detector is further effective to carry out differentiation for smoothing of the bio-signal data to identify a range in the vicinity of a differential waveform gradient at zero degrees to thereby detect the peak value from the original waveform corresponding to the range identified.

6. The human condition evaluation system according to claim 2, wherein said Lyapunov exponent peak value detector is further effective to carry out differentiation for smoothing of the Lyapunov exponent to identify a range in the vicinity of a differential waveform gradient at zero degrees to thereby detect the peak value from the original waveform corresponding to the range identified.

7. The human condition evaluation system according to claim 1, wherein said power value calculator is further effective to calculate as a power value, a difference between an average maximum peak value and an average minimum peak value both in a certain time range of the bio-signal data.

8. The human condition evaluation system according to claim 1, wherein the gradient of the power value or of the gradient of the Lyapunov exponent calculated by said gradient calculator is a value obtained by a least-squares method.

9. The human condition evaluation system according to claim 1, further comprising a frequency analyzer effective to perform frequency analysis on the gradient of the power value or the gradient of the Lyapunov exponent to determine a human condition.

10. The human condition evaluation system according to claim 1, further comprising an output means for actuating an awakening means for awakening a person when said comparative determinator detects the predictive signal for falling asleep from the active state to the sleep state.

11. A computer program, embodied on a computer readable medium, for letting a computer execute a process of evaluating a human condition by analyzing a bio-signal data detected by a bio-signal measurement in a bio-signal of a human, the process comprising:

detecting a peak value for each cycle of an original waveform of the bio-signal data, calculating a difference between the peak value at an upper limit side and the peak value at a lower limit side for each prescribed time range using respective peak values obtained by said bio-signal peak value detection step to thereby set the difference as a power value, obtaining a gradient of the power value with regard to time base in a certain time range by performing slide calculation a prescribed number of times at a prescribed overlap rate with regard to the prescribed time, and comparatively determining whether a sudden drop state of the gradient of the power value exists or not in time-series change in gradient of the power value obtained by performing the slide calculation to thereby determine the time range in which the sudden drop state appears to be a predictive signal for falling asleep from an active state into a sleep state.

12. The computer program according to claim 11, further comprising:

calculating a Lyapunov exponent by performing chaos theory analysis on the bio-signal data, and detecting a peak value for each cycle of a time-series change waveform of the Lyapunov exponent calculated by said Lyapunov exponent calculation step, wherein said gradient calculation step includes obtaining, in addition to the gradient of the power value, a gradient of respective peak values of the Lyapunov exponent with regard to time base in a certain time range obtained by said Lyapunov exponent peak value detection step, and wherein said comparative determination step comparatively determines whether a sudden drop state exists or not in at least one of the time-series changes in the gradients of the power value and the Lyapunov exponent obtained by performing the slide calculation to determine a range in which the sudden drop state appears to be the predictive signal for falling asleep from the active state into the sleep state.

13. The computer program according to claim 12, wherein said comparative determination step compares the time-series changes in the gradients of the power value and the Lyapunov exponent which are obtained by performing the slide calculation of said gradient calculation step, and determines whether the gradients of the power value and the Lyapunov exponent are in opposite phases with each other or not before or in the range in which the sudden drop appears in the gradient of the power value or in the gradient of the Lyapunov exponent, and in the case where the sudden drop in the gradient of the power value or in the gradient of the Lyapunov exponent appears together with the opposite phase, said comparative determination step includes determination of the range to be the predictive signal for falling asleep from the active state into the sleep state.

14. The computer program according to claim 11, wherein said comparative determination step includes determining that the transition into the sleep state is made when each time-series change in the gradient of the power value or of the Lyapunov exponent appears at a low amplitude on the whole, after the sudden drop appears in the gradient of the power value or in the gradient Lyapunov exponent.

15. The computer program according to claim 11, further comprising a step of performing frequency analysis on the gradient of the power value or the gradient of the Lyapunov exponent to determine the state of the human condition.

16. The computer program according to claim 11, further comprising actuating an awakening means for awakening a person when the predictive signal for falling asleep from the active state to the sleep state is detected by said comparative determination step.

* * * * *